(12) United States Patent
Zapol et al.

(10) Patent No.: US 10,239,038 B2
(45) Date of Patent: Mar. 26, 2019

(54) SYSTEMS AND METHODS FOR A COOLED NITRIC OXIDE GENERATOR

(71) Applicant: The General Hospital Corporation, Boston, MA (US)

(72) Inventors: Warren Zapol, Cambridge, MA (US); Binglan Yu, Lexington, MA (US)

(73) Assignee: The General Hospital Corporation, Boston, MA (US)

(*) Notice: Subject to any disclaimer, the term of this patent is extended or adjusted under 35 U.S.C. 154(b) by 0 days.

(21) Appl. No.: 15/941,367

(22) Filed: Mar. 30, 2018

(65) Prior Publication Data

US 2018/0280920 A1    Oct. 4, 2018

Related U.S. Application Data

(60) Provisional application No. 62/558,882, filed on Sep. 15, 2017, provisional application No. 62/480,320, filed on Mar. 31, 2017.

(51) Int. Cl.

| | |
|---|---|
| *B01J 19/08* | (2006.01) |
| *C01B 21/32* | (2006.01) |
| *A61K 33/00* | (2006.01) |
| *A61P 9/12* | (2006.01) |
| *A61K 9/00* | (2006.01) |

(52) U.S. Cl.
CPC ............ *B01J 19/088* (2013.01); *A61K 9/007* (2013.01); *A61K 33/00* (2013.01); *A61P 9/12* (2018.01); *C01B 21/32* (2013.01); *B01J 2219/0809* (2013.01); *B01J 2219/0839* (2013.01); *B01J 2219/0841* (2013.01); *B01J 2219/0843* (2013.01); *B01J 2219/0871* (2013.01); *B01J 2219/0875* (2013.01); *B01J 2219/0898* (2013.01)

(58) Field of Classification Search
None
See application file for complete search history.

(56) References Cited

U.S. PATENT DOCUMENTS

| | | |
|---|---|---|
| 2,485,481 A | 10/1949 | Cotton |
| 2,525,938 A | 10/1950 | Peck |
| 2,684,448 A | 7/1954 | Nilles, Jr. |

(Continued)

FOREIGN PATENT DOCUMENTS

| | | |
|---|---|---|
| CN | 1099997 A | 3/1995 |
| CN | 1730115 A | 2/2006 |

(Continued)

OTHER PUBLICATIONS

Mok, et al., Application of Positive Pulsed Corona Discharge to Removal of SO2 and NOx, Proceedings, ICESP VII, Sep. 20-25, 1998, Kyongju, Korea, 8 pages.

(Continued)

*Primary Examiner* — Kishor Mayekar
(74) *Attorney, Agent, or Firm* — Quarles & Brady LLP

(57) ABSTRACT

Systems and methods for a nitric oxide (NO) generation system are provided. In particular, the present disclosure provide an NO generation system that is configured to be cooled to maintain an NO generator of the system at or below temperatures safe for patient use and contact. In some non-limiting examples, the NO generation system may include a pump configured to furnish a fluid (e.g., a gas) toward and/or through the NO generator to provide cooling thereto.

44 Claims, 14 Drawing Sheets

(56) References Cited

U.S. PATENT DOCUMENTS

| | | | |
|---|---|---|---|
| 3,225,309 A | 12/1965 | Phelps | |
| 4,287,040 A | 9/1981 | Alamaro | |
| 4,500,563 A | 2/1985 | Ellenberger et al. | |
| 4,505,795 A | 3/1985 | Alamaro | |
| 4,695,358 A | 9/1987 | Mizuno et al. | |
| 4,705,670 A | 11/1987 | O'Hare | |
| 4,816,229 A | 3/1989 | Jensen et al. | |
| 4,877,589 A | 10/1989 | O'Hare | |
| 5,285,372 A | 2/1994 | Huynh et al. | |
| 5,378,436 A | 1/1995 | Endoh et al. | |
| 5,396,882 A | 3/1995 | Zapol | |
| 5,471,977 A | 12/1995 | Olsson et al. | |
| 5,485,827 A | 1/1996 | Zapol et al. | |
| 5,546,935 A | 8/1996 | Champeau | |
| 5,558,083 A | 9/1996 | Bathe et al. | |
| 5,573,733 A | 11/1996 | Salama | |
| 5,692,495 A | 12/1997 | Sheu | |
| 5,732,693 A | 3/1998 | Bathe et al. | |
| 5,752,504 A | 5/1998 | Bathe | |
| 5,839,433 A | 11/1998 | Higenbottam | |
| 5,845,633 A | 12/1998 | Psaros | |
| 6,089,229 A | 7/2000 | Bathe et al. | |
| 6,109,260 A | 8/2000 | Bathe | |
| 6,125,846 A | 10/2000 | Bathe et al. | |
| 6,164,276 A | 12/2000 | Bathe et al. | |
| 6,224,653 B1 | 5/2001 | Shvedchikov et al. | |
| 6,250,302 B1 | 6/2001 | Rantala | |
| 6,296,827 B1 | 10/2001 | Castor et al. | |
| 6,536,429 B1 | 3/2003 | Pavlov et al. | |
| 6,668,828 B1 | 12/2003 | Figley et al. | |
| 6,758,214 B2 | 7/2004 | Fine et al. | |
| 6,920,876 B2 | 7/2005 | Miller et al. | |
| 6,955,171 B1 | 10/2005 | Figley et al. | |
| 6,955,790 B2 | 10/2005 | Castor et al. | |
| 6,986,351 B2 | 1/2006 | Figley et al. | |
| 7,025,869 B2 | 4/2006 | Fine et al. | |
| 7,040,313 B2 | 5/2006 | Fine et al. | |
| 7,122,018 B2 | 10/2006 | Stenzler et al. | |
| 7,220,393 B2 | 5/2007 | Miller et al. | |
| 7,255,105 B2 | 8/2007 | Figley et al. | |
| 7,335,181 B2 | 2/2008 | Miller et al. | |
| 7,485,324 B2 | 2/2009 | Miller et al. | |
| 7,498,000 B2 | 3/2009 | Pekshev et al. | |
| 7,516,742 B2 | 4/2009 | Stenzler et al. | |
| 7,520,866 B2 | 4/2009 | Stenzler et al. | |
| 7,531,133 B2 | 5/2009 | Hole et al. | |
| 7,560,076 B2 | 7/2009 | Rounbehler et al. | |
| 7,589,473 B2 | 9/2009 | Suslov | |
| 7,744,812 B2 | 6/2010 | Witherspoon et al. | |
| 7,861,717 B1 | 1/2011 | Krebs | |
| 7,955,294 B2 | 6/2011 | Stenzler et al. | |
| 8,030,849 B2 | 10/2011 | Suslov | |
| 8,043,252 B2 | 10/2011 | Miller et al. | |
| 8,079,998 B2 | 12/2011 | Hole et al. | |
| 8,151,791 B2 | 4/2012 | Arlow et al. | |
| 8,282,966 B2 | 10/2012 | Baldassarre et al. | |
| 8,291,904 B2 | 10/2012 | Bathe et al. | |
| 8,293,284 B2 | 10/2012 | Baldassarre et al. | |
| 8,344,627 B1 | 1/2013 | Hooke et al. | |
| 8,431,163 B2 | 4/2013 | Baldassarre et al. | |
| 8,518,457 B2 | 8/2013 | Miller et al. | |
| 8,573,209 B2 | 11/2013 | Bathe et al. | |
| 8,573,210 B2 | 11/2013 | Bathe et al. | |
| 8,574,531 B2 | 11/2013 | Miller et al. | |
| 8,717,733 B2 | 5/2014 | Gefter et al. | |
| 8,776,794 B2 | 7/2014 | Bathe et al. | |
| 8,776,795 B2 | 7/2014 | Bathe et al. | |
| 8,790,715 B2 | 7/2014 | Montgomery et al. | |
| 8,795,222 B2 | 8/2014 | Stenzler et al. | |
| 8,795,741 B2 | 8/2014 | Baldassarre | |
| 8,821,828 B2 | 9/2014 | Hilbig et al. | |
| 8,846,112 B2 | 9/2014 | Baldassarre | |
| 9,095,534 B2 | 8/2015 | Stenzler et al. | |
| 9,265,911 B2 | 2/2016 | Bathe et al. | |
| 9,279,794 B2 | 3/2016 | Tolmie et al. | |
| 9,295,802 B2 | 3/2016 | Bathe et al. | |
| 9,408,993 B2 | 8/2016 | Bathe et al. | |
| 9,573,110 B2 | 2/2017 | Montgomery et al. | |
| 9,770,570 B2 | 9/2017 | Schnitman et al. | |
| 9,982,354 B2 | 5/2018 | Kim | |
| 2001/0031230 A1 | 10/2001 | Castor et al. | |
| 2004/0019274 A1 | 1/2004 | Galloway, Jr. et al. | |
| 2004/0028753 A1 | 2/2004 | Hedenstierna et al. | |
| 2004/0031248 A1 | 2/2004 | Lindsey | |
| 2004/0181149 A1 | 9/2004 | Langlotz et al. | |
| 2005/0172971 A1 | 8/2005 | Kolobow et al. | |
| 2005/0218007 A1 | 10/2005 | Pekshev et al. | |
| 2005/0263150 A1 | 12/2005 | Chathampally et al. | |
| 2005/0281465 A1 | 12/2005 | Marquart et al. | |
| 2006/0025700 A1 | 2/2006 | Fallik | |
| 2006/0172018 A1 | 8/2006 | Fine et al. | |
| 2006/0276844 A1 | 12/2006 | Alon et al. | |
| 2007/0151561 A1 | 7/2007 | Laurila | |
| 2007/0190184 A1 | 8/2007 | Montgomery et al. | |
| 2008/0017030 A1 | 1/2008 | Fleck | |
| 2008/0078382 A1 | 4/2008 | LeMahieu et al. | |
| 2008/0135044 A1 | 6/2008 | Freitag et al. | |
| 2008/0202509 A1 | 8/2008 | Dillon et al. | |
| 2010/0189808 A1 | 7/2010 | Gupta et al. | |
| 2010/0275911 A1 | 11/2010 | Arlow et al. | |
| 2012/0279500 A1 | 11/2012 | Singvogel et al. | |
| 2012/0296265 A1 | 11/2012 | Dobrynin et al. | |
| 2013/0123801 A1 | 5/2013 | Umasuthan et al. | |
| 2013/0150863 A1 | 6/2013 | Baumgartner | |
| 2014/0031668 A1 | 1/2014 | Mobasser et al. | |
| 2014/0158121 A1 | 6/2014 | Flanagan et al. | |
| 2014/0251787 A1 | 9/2014 | Montgomery et al. | |
| 2014/0363525 A1 | 12/2014 | Montgomery et al. | |
| 2015/0000659 A1 | 1/2015 | Martin | |
| 2015/0004248 A1 | 1/2015 | Morfill et al. | |
| 2015/0034084 A1 | 2/2015 | Av-Gay et al. | |
| 2015/0044305 A1 | 2/2015 | Av-Gay et al. | |
| 2015/0072023 A1 | 3/2015 | Greenberg et al. | |
| 2015/0090261 A1 | 4/2015 | Crosbie | |
| 2015/0174158 A1 | 6/2015 | Av-Gay et al. | |
| 2015/0272988 A1 | 10/2015 | Av-Gay et al. | |
| 2016/0022731 A1 | 1/2016 | Av-Gay et al. | |
| 2016/0030699 A1 | 2/2016 | Zapol et al. | |
| 2016/0038710 A1 | 2/2016 | Zapol et al. | |
| 2016/0183841 A1 | 6/2016 | Duindam et al. | |
| 2016/0191887 A1 | 6/2016 | Casas | |
| 2016/0228670 A1 | 8/2016 | Av-Gay et al. | |
| 2016/0243328 A1 | 8/2016 | Tolmie et al. | |
| 2016/0324580 A1 | 11/2016 | Esterberg | |
| 2016/0367775 A1 | 12/2016 | Tolmie et al. | |
| 2017/0014571 A1 | 1/2017 | Deem et al. | |
| 2017/0014591 A1 | 1/2017 | Tolmie et al. | |
| 2017/0014592 A1 | 1/2017 | Tolmie et al. | |
| 2017/0021124 A1 | 1/2017 | Tolmie et al. | |
| 2017/0065631 A1 | 3/2017 | Av-Gay et al. | |
| 2017/0143758 A1 | 5/2017 | Greenberg et al. | |
| 2017/0239289 A1 | 8/2017 | Av-Gay et al. | |
| 2018/0049622 A1 | 2/2018 | Ryan et al. | |
| 2018/0125883 A1 | 5/2018 | Av-Gay et al. | |
| 2018/0133246 A1 | 5/2018 | Av-Gay et al. | |

FOREIGN PATENT DOCUMENTS

| | | |
|---|---|---|
| CN | 101828432 A | 9/2010 |
| EP | 0621051 A2 | 10/1994 |
| EP | 1036758 A1 | 9/2000 |
| EP | 1854494 A1 | 11/2007 |
| EP | 2151554 A1 | 2/2010 |
| JP | H04132560 A | 5/1992 |
| JP | 2000102616 A | 4/2000 |
| JP | 2006273677 A | 10/2006 |
| WO | 2004032719 A2 | 4/2004 |
| WO | 2011002606 A1 | 1/2011 |
| WO | 2012094008 A1 | 7/2012 |
| WO | 2013052548 A2 | 4/2013 |
| WO | 2013070712 A1 | 5/2013 |
| WO | 2013181179 A1 | 12/2013 |
| WO | 2014085719 A1 | 6/2014 |
| WO | 2014143842 A1 | 9/2014 |

(56) References Cited

FOREIGN PATENT DOCUMENTS

| WO | 2014144151 A1 | 9/2014 |
| WO | 2015066278 A1 | 5/2015 |
| WO | 2015127085 A1 | 8/2015 |

OTHER PUBLICATIONS

Keshav, Using Plasmas for High-Speed Flow Control and Combustion Control, Dissertation for Degree of Doctor of Philosophy, The Ohio State University, 2008, 268 pages.
Namihira, et al., Production of Nitric Oxide Using a Pulsed Arc Discharge, IEEE Transactions on Plasma Science, 2002, 30(5):1993-1998.
PCT International Search Report, PCT/US2014/028439, dated Jul. 24, 2014.
PCT International Preliminary Report on Patentability, PCT/US2014/028439, dated Sep. 15, 2015.
PCT International Search Report, PCT/US2014/027986, dated Jul. 17, 2014.
PCT International Preliminary Report on Patentability, PCT/US2014/027986, dated Sep. 15, 2015.
PCT International Search Report and Written Opinion, PCT/US2015/056443, dated Jan. 6, 2016.

|  | Ni⁶⁰ (ppb) | Ir¹⁹³ (ppb) | Pt¹⁹⁵ (ppb) |
|---|---|---|---|
| Without scavenger & filter | 40.3 | 0.029 | 0.001 |
| With scavenger & filter | 0.72 | 0.012 | 0.002 |
| With scavenger & 2 filters | 0.35 | 0.010 | 0.002 |
| Scavenger only | 1.7 | 0.015 | 0.003 |
| Filter only | 0.3 | 0.010 | 0.002 |

FIG. 13

SYSTEMS AND METHODS FOR A COOLED NITRIC OXIDE GENERATOR

CROSS-REFERENCES TO RELATED APPLICATIONS

The present application is based on and claims priority to U.S. Provisional Patent Application No. 62/480,320, filed on Mar. 31, 2017 and U.S. Provisional Patent Application No. 62/558,882, filed on Sep. 15, 2017. Each of which is incorporated herein by reference.

STATEMENT REGARDING FEDERALLY SPONSORED RESEARCH

Not Applicable.

BACKGROUND

The present disclosure relates generally to electric plasma synthesis of nitric oxide (NO) from gases and, more specifically, to systems and methods for a cooled NO generator to be used in medical applications.

NO is a crucial mediator of many biological systems, and is known to selectively regulate pulmonary arterial and systemic pressure, help the immune system kill invading parasites that enter cells, inhibit the division of cancer cells, transmit signals between brain cells, and contribute to the death of brain cells that debilitates people with strokes or heart attacks, among other things. NO mediates the relaxation of smooth muscle present, for example, in the walls of blood vessels, bronchi, the gastrointestinal tract, and urogenital tract. Administration of NO gas to the lung by inhalation has been shown to produce localized smooth muscle relaxation within the lung's blood vessels and is widely used to treat pulmonary hypertension, pneumonia, hypoxemic respiratory failure of a term newborn, etc. without producing systemic side effects such as systemic vasodilation and hypotension.

Inhaling NO can immediately produce potent and selective pulmonary vasodilation that improves the matching of ventilation with perfusion, thereby increasing an injured lung's oxygen transport efficiency, and breathing NO can raise the arterial oxygen tension. Breathing NO produces the rapid onset of pulmonary vasodilator action occurring within seconds of commencing breathing with the absence of systemic vasodilatation. Once inhaled, NO diffuses through the pulmonary vasculature into the bloodstream, where it is rapidly inactivated by combination with oxyhemoglobin (the NO dioxygenation reaction). Therefore, the vasodilatory effects of inhaled NO are limited to the lung in the treatment of acute and chronic pulmonary hypertension. Inhaled NO can also be used to prevent ischemia reperfusion injury after percutaneous coronary intervention in adults with heart attacks. Furthermore, inhaled NO can produce systemic anti-inflammatory and anti-platelet effects by increasing the levels of circulating NO biometabolites (including cyclic guanosine monophosphate) and by other mechanisms, such as the oxidation of circulating ferrous hemoglobin to ferric hemoglobin (methemoglobin) in the plasma. Further still, NO has known anti-microbial activity.

BRIEF SUMMARY

In one aspect, the present disclosure provides a nitric oxide generation system that includes a nitric oxide generator. The nitric oxide generator includes a housing having a first end and a generally open second end, a pair of electrodes enclosed within the housing, and a reaction chamber defined between the pair of electrodes and the housing. The nitric oxide generation system further includes a scavenger housing having a scavenger and a filter arranged therein. The scavenger housing is configured to be removably attached to the second end of the housing. The nitric oxide generation system further includes a power supply connected to the pair of electrodes, and a controller in communication with the pump and the power supply. The controller is configured to selectively instruct the power supply to provide power to the pair of electrodes to generate one or more electric discharges therebetween to generate nitric oxide within the reaction chamber. The nitric oxide generation system further includes a pump configured to provide fluid flow and a flow tube configured to provide fluid communication between the pump and the reaction chamber. The fluid flow provided from the pump to the reaction chamber is configured to cool the nitric oxide generator and aid in the diffusion of the generated nitric oxide from the reaction chamber.

In one aspect, the present disclosure provides an apparatus for generating nitric oxide that includes a housing having a first end, a generally open second end, and a cavity arranged between the first end and the second end, a pair of electrodes arranged within the cavity of the housing, and a reaction chamber defined between the pair of electrodes and the housing. The pair of electrodes are configured to generate one or more electric discharges therebetween to generate nitric oxide within the reaction chamber. The apparatus further includes a scavenger housing having a scavenger and a filter arranged therein. The scavenger housing is configured to be removably attached to the second end of the housing. The apparatus further includes a flow tube extending through the housing and into the reaction chamber to provide fluid communication between a pump and the reaction chamber. The fluid flow provided from the pump to the reaction chamber is configured to cool to the nitric oxide generator and aid in the diffusion of the generated nitric oxide from the reaction chamber.

In one aspect, the present disclosure provides a method of cooling a nitric oxide generator configured to electrically generate nitric oxide gas via electric plasma discharge between a pair of electrodes. The nitric oxide generator includes a housing enclosing the pair of electrodes and defining a reaction chamber between the pair of electrodes and the housing. The method includes providing a pump configured to provide fluid flow, connecting a flow tube between the pump and the reaction chamber to provide fluid communication therebetween, and flowing fluid from the pump to the reaction chamber along the flow tube, thereby cooling the nitric oxide generator.

The foregoing and other aspects and advantages of the disclosure will appear from the following description. In the description, reference is made to the accompanying drawings, which form a part hereof, and in which there is shown by way of illustration a preferred configuration of the disclosure. Such configuration does not necessarily represent the full scope of the disclosure, however, and reference is made therefore to the claims and herein for interpreting the scope of the disclosure.

BRIEF DESCRIPTION OF DRAWINGS

The invention will be better understood and features, aspects and advantages other than those set forth above will become apparent when consideration is given to the following detailed description thereof. Such detailed description makes reference to the following drawings.

FIG. 13 is a table illustrating a concentration of nickel, iridium, and platinum output by the prototype generator of FIG. 8A using various scavenger and filter combinations during a twenty-four hour test generating 40 ppm nitric oxide (NO).

DETAILED DESCRIPTION

The use of the term "fluid" herein relates to a phase of matter and may relate to a liquid, a gas, or a two-phase liquid and gas.

The use of the terms "downstream" and "upstream" herein are terms that indicate direction relative to the flow of a fluid. The term "downstream" corresponds to the direction of fluid flow, while the term "upstream" refers to the direction opposite or against the direction of fluid flow.

As will be described, the present disclosure provides a nitric oxide (NO) generation system that is a fully portable, lightweight, and can reliably and safely generate NO at concentrations useful in medical applications and at the point-of-care. Generally, some non-limiting examples of the present disclosure provide an NO generation system that is configured to be cooled to maintain an NO generator of the system at or below temperatures safe for patient use and contact. In some non-limiting examples, the NO generation system may include a pump configured to furnish a fluid (e.g., a gas) toward and/or through the NO generator to provide cooling thereto. The fluid flow provided by the pump may also increase the efficiency of NO generation, facilitate the diffusion of freshly generated NO, and aid in preventing at least a portion of exhaled carbon dioxide ($CO_2$) from entering the system.

Figure 1:
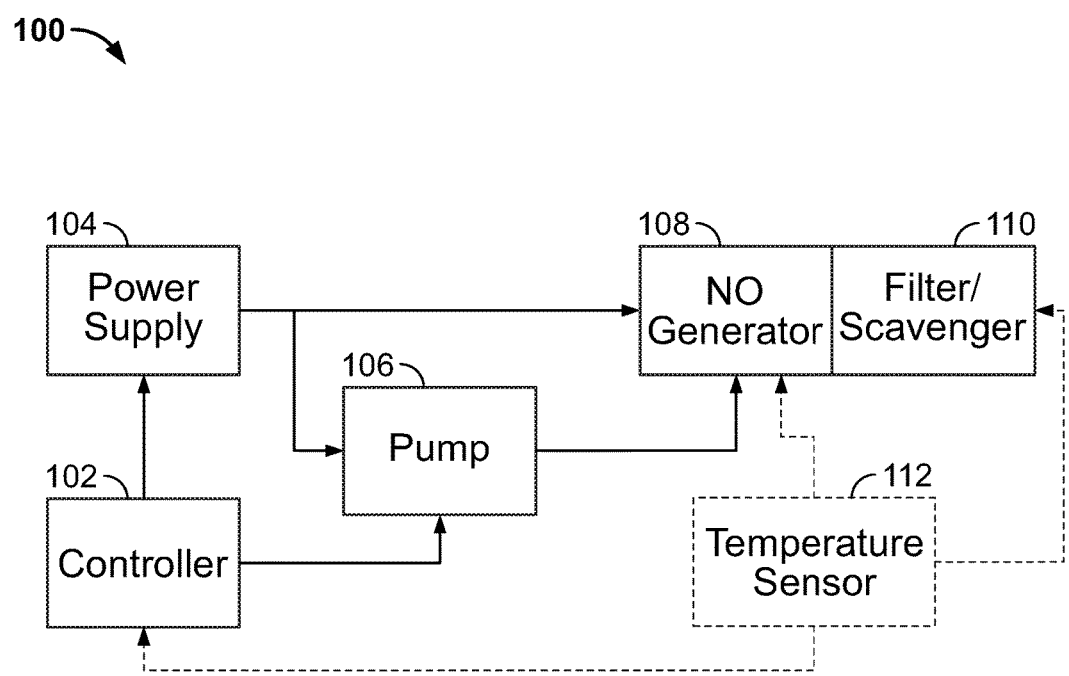
FIG. 1 is a schematic illustration of a nitric oxide generation system according to one aspect of the present disclosure.

FIG. 1 illustrates one non-limiting example of an NO generation system 100 according to the present disclosure. The NO generation system includes a controller 102, a power supply 104, a pump 106, an NO generator 108, and a filter/scavenger 110. In some non-limiting examples, the power supply 104 may be a resonant power supply. The controller 102 is in communication with the power supply 104 and the pump 106. In some non-limiting examples, the controller 102 may be configured to selectively instruct the power supply 104 to provide power to the NO generator 108, which results in the generation of a desired concentration of NO gas to be supplied to a patient. For example, the controller 102 may be configured to selectively trigger the power supply 104 based on one or more inputs, such as, an inspiration event. The inspiration event may be detected via one or more characteristics of the patient's respiration. For example, fluid flow rate, temperature, pressure, oxygen ($O_2$) concentration, $CO_2$ concentration, thoracic volume, etc. Alternatively or additionally, the controller 102 may be configured to receive one or more inputs from a ventilator to determine when to trigger the NO generator 108 during or before an inspiration event.

In some non-limiting examples, the controller 102 may be configured to instruct the NO generator 108 to produce a desired concentration of NO for a predetermined about of time during or before each inspiration event. In some non-limiting examples, the controller 102 may be configured to instruct the NO generator 108 to produce a desired concentration of NO for a predetermined amount of time during or before every other inspiration event. In some non-limiting examples, the controller 102 may be configured to instruct the NO generator 108 to produce a desired concentration of NO for a predetermined amount of time during or before every third inspiration event, or at larger gaps between inspiration events (e.g., every fourth, fifth, or sixth inspiration event, etc.).

In some non-limiting examples, the power supply 104 may be configured to provide power to the pump 106. In these non-limiting examples, the controller 102 may be configured to selectively instruct the power supply 104 to provide power to the pump 106 to facilitate fluid flow into and/or through the NO generator 108. In some non-limiting examples, the pump 106 may be integrated with a native power supply or may be powered via another external power supply separate from the power supply 104. In these non-limiting examples, the controller 102 may be configured to selectively instruct the pump 106 to furnish fluid flow (from low to high ml/min or vice versa) into and/or through the NO generator 108.

The controller 102 may be configured to control a fluid flow rate provided by the pump 106 to the NO generator 108. In some non-limiting examples, the controller 102 may be configured to maintain a temperature of the NO generator 108 within a desired temperature range by controlling the fluid flow rate provided by the pump 106. For example, the controller 102 may be in communication with a temperature sensor 112 that is configured to measure a temperature of the NO generator 108 and may be configured to control the fluid flow rate provided by the pump 106 based on the temperature measured by the temperature sensor 112. Alternatively or additionally, the temperature sensor 112 may be configured to measure a temperature of the fluid flow exiting the filter/scavenger 110 being provided to the patient, and the controller 102 may be configured to control the fluid flow rate provided by the pump 106 to maintain the exiting fluid flow to the patient within a desired temperature range.

The NO generator 108 is configured to generate a desired concentration of NO gas, upon being supplied with power from the power supply 104, from ambient gases within the NO generator 108 and/or gas supplied by the pump 106. For example, the NO generator 108 may include one or more pairs of electrodes that are configured to generate a plasma via electric discharge therebetween. NO gas may be synthesized from the $O_2$ and nitrogen ($N_2$) in the ambient or higher pressure gases within the plasma generated via the electrode discharge. In some non-limiting examples, a waveform (e.g., square wave, etc.) provided to the NO generator 108 by the power supply 104 may control a concentration of NO generated thereby. In some non-limiting examples, the NO concentration generated by the NO generator 108 may be measured and the controller 102 may control the power supply 104 to maintain the NO concentration with in a desired range.

In general, the filter/scavenger 110 may include at least one filter configured to prevent/filter particles prior to the NO-laden gas entering the airway of a patient and a scavenger configured to control, or limit, a concentration of undesirable byproducts (e.g., $NO_2$ and $O_3$) produced by the NO generator 108. In some non-limiting examples, the filter/scavenger 110 may be integrated into a unitary component that may be removably attached to the NO generator 108. For example, the filter/scavenger 110 may be a replaceable component that is configured to be installed on the NO generator 108 and removed once the scavenger has been exhausted. In some non-limiting examples, the filter/scavenger 110 may be removably attached to the NO generator 108 via, screws, a quick-disconnect (snap on/off), a keyed feature, a removable adhesive, and/or threads.

The NO generation system 100 may be integrated into a lightweight and portable device that provides point-of-care treatment, for example, to hypoxic babies. In some non-limiting examples, the NO generator 108 may be installed in or near an endotracheal tube that in installed in the airway of a patient. In some non-limiting examples, the NO generator 108 may be installed directly in the airway of a patient as close as possible to a mouth piece, in the inspiratory limb. However, the system 100 may be used with any of a variety of subjects, which may include a human, other mammal, or other animal, or may be used in other applications that do not include a subject.

Figure 2:
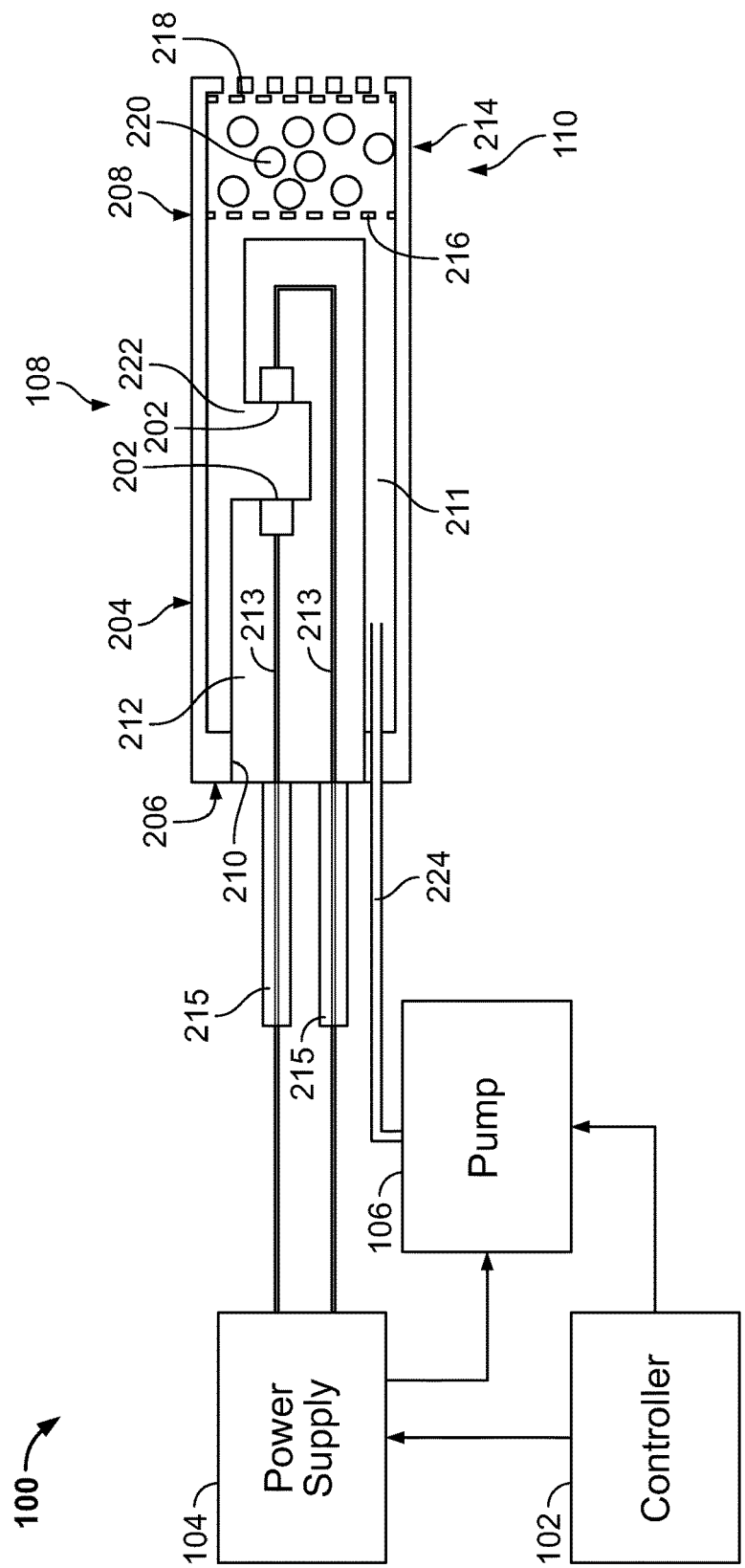
FIG. 2 is a detailed schematic of a nitric oxide generator within the nitric oxide generation system of FIG. 1 according to one aspect of the present disclosure.

Turning to FIG. 2, in one non-limiting example, the NO generator 108 includes a pair of electrodes 202 arranged within a housing 204. The electrodes 202 can be fabricated from or plated with tungsten carbide, carbon, iridium, titanium, platinum, rhenium, or an alloy of the aforementioned materials, or other noble inert metals. In one non-limiting example, the electrodes 202 are fabricated from or plated with iridium due to a lower ratio of $NO_2$ to NO generated by iridium when compared to other metals, as described in International Patent Application No. PCT/US2015/056443 ('443 International Application), which is hereby incorporated herein by reference. In other non-limiting examples, the NO generator 108 may include two or more pairs of electrodes 202. The electrodes 202 are configured to create a plasma therebetween upon electric discharge. The plasma generated by the electrodes 202 generates NO gas, as long as nitrogen and oxygen are present in the atmosphere in which the NO generator 108 is placed.

The housing 204 includes a first end 206 and a second end 208 longitudinally opposing one another. In some non-limiting examples, the housing 204 may be fabricated from a metal material (e.g., aluminum). The first end 206 includes an aperture 210 that provides access to a cavity 211 formed by an interior of the housing 204. The aperture 210 may be dimensioned to receive an electrode insulator 212. A pair of high voltage wires 213 extend through the electrode insulator 212 and connect the electrodes 202 to the power supply 104. The high voltage wires 213 may include wire insulation 215 except when located within the electrode insulator 212 (e.g. a ceramic material), which acts to electrically insulate and prevent shorting. In some non-limiting examples, the wire insulation 215 may be a molded component that includes apertures for the wires 213 and a flow tube 224 to extend therethrough. In these non-limiting examples, the wire insulation 215 may be fabricated from an electrical insulator and may be configured to be attached to the first end 206 of the housing 204.

In some non-limiting examples, the second end 208 may define a generally open end that is configured to removably attach to a scavenger housing 214. In these non-limiting examples, the scavenger housing 214 may include a first filter 216, a second filter 218, and a scavenger 220 arranged between the first filter 216 and the second filter 218. When assembled, as illustrated in FIG. 2, the first filter 216 may be in engagement with the second end 208 of the housing 204. In some non-limiting examples, the scavenger housing 214 may be removably attached to the housing 204 via, screws, a quick-disconnect, a keyed feature, a removable adhesive, and/or threads.

In some non-limiting examples, the first filter 216 may be integrated into the housing 204 and attached to the second end 208 thereof. In these non-limiting examples, the scavenger housing 214 may include the second filter 218 and the scavenger 220.

The first and second filters 216 and 218 may be configured to filter particles prior to the gas within the housing 204 entering the airway of the patient. For example, the first and second filters 216 and 218 may prevent fragments from the scavenger 220 and/or particles/vapors that boil off from the electrodes 202 due to the high temperatures generated during discharge from entering the airway of a patient. In the illustrated non-limiting example, the NO generator 108 includes one filter arranged upstream of the scavenger 220 and another filter arranged downstream of the scavenger 220. In some non-limiting examples, the first and second filters 216 and 218 may be configured to filter particles with a diameter larger than approximately 0.22 micrometers (μm). In one configuration, the first and second filters 216 and 218 may be a high efficiency particulate absorption (HEPA) filters. As described in the '443 International Application, a 0.22 μm particle filter arranged upstream of a patient is sufficient to remove electrode fragments that erode and vaporize during operation. It should be known that the particle size filtered by the first and second filters 216 and 218 is not meant to be limiting in any way, and alternative particle filters that filter different particle sizes are within the scope of the present disclosure. However, the particle size filtered by the first and second filters 216 and 218 should be sufficiently small to maintain the safety and health of a patient.

When the scavenger housing 214 is attached to the housing 204, the scavenger 220 is configured to be arranged downstream of the electrodes 202. In operation, the scavenger 220 may be configured to control undesirable byproducts (e.g., $NO_2$ and $O_3$) produced by the system 100. In one non-limiting example, the scavenger 220 may be fabricated from calcium hydroxide ($Ca(OH)_2$). In another non-limiting example, the scavenger 220 may be a reductant scavenger composed of any reductant (e.g., ascorbic acid). In some non-limiting examples, NO generation system 100 may be configured to efficiently generate NO gas for inhalation by a patient by triggering on inspiration of the patient, which may reduce the power requirements of the system 100 and facilitate the use of a small scavenger 220. For example, the scavenger 220 may be less than approximately 2 grams (g). In some non-limiting examples, the scavenger 220 may be between approximately 1 g and approximately 2 g. In some non-limiting examples, the scavenger 220 may be approximately 1.6 g. In some non-limiting examples, the scavenger 220 may be less than approximately 1 g. In some non-limiting examples, the scavenger 220 may be between approximately 0.1 g and approximately 1 g. In some non-limiting examples, the scavenger 220 may be approximately 0.8 g.

When assembled, a flow path may be defined through the NO generator 108 that facilitates the delivery of generated NO-laden gas to a patient. The flow path may extend from a reaction chamber 222 downstream through the first filter 216, the scavenger 220, and to the second filter 218. In some non-limiting examples, the second filter 218 may be an outlet of the flow path. In some non-limiting examples, the scavenger housing 214 may include a perforated outlet wall that is configured to secure the second filter 218 therein but allow fluid to flow therethrough.

The reaction chamber 222 may be defined as a portion of the cavity 211 in the radial clearance between the electrode insulator 212 and the inner surface of the housing 204. Ambient gases within the reaction chamber 222 may undergo a chemical reaction following an electric plasma discharge between the electrodes 202 and, in the presence of nitrogen and oxygen, NO gas may be generated to be supplied to a patient at a given concentration. As described herein, the NO generation system 100 may be triggered to only generate NO gas upon or before selective inspiration events of a patient to reduce power consumption and size of the scavenger 220. However, the electric plasma discharge between the electrodes 202 does generate heat, which may result in heating of the NO generator 108 during operation. To reduce the heating effect and control a temperature of the NO generator 108, a flow tube 224 is arranged to provide fluid communication between the reaction chamber 222 and the pump 106. In the illustrated non-limiting example, the flow tube 224 extends generally axially into the first end 206 of the housing 204 at a radial location between the electrode insulator 212 and the inner surface of the housing 204.

Figure 3:
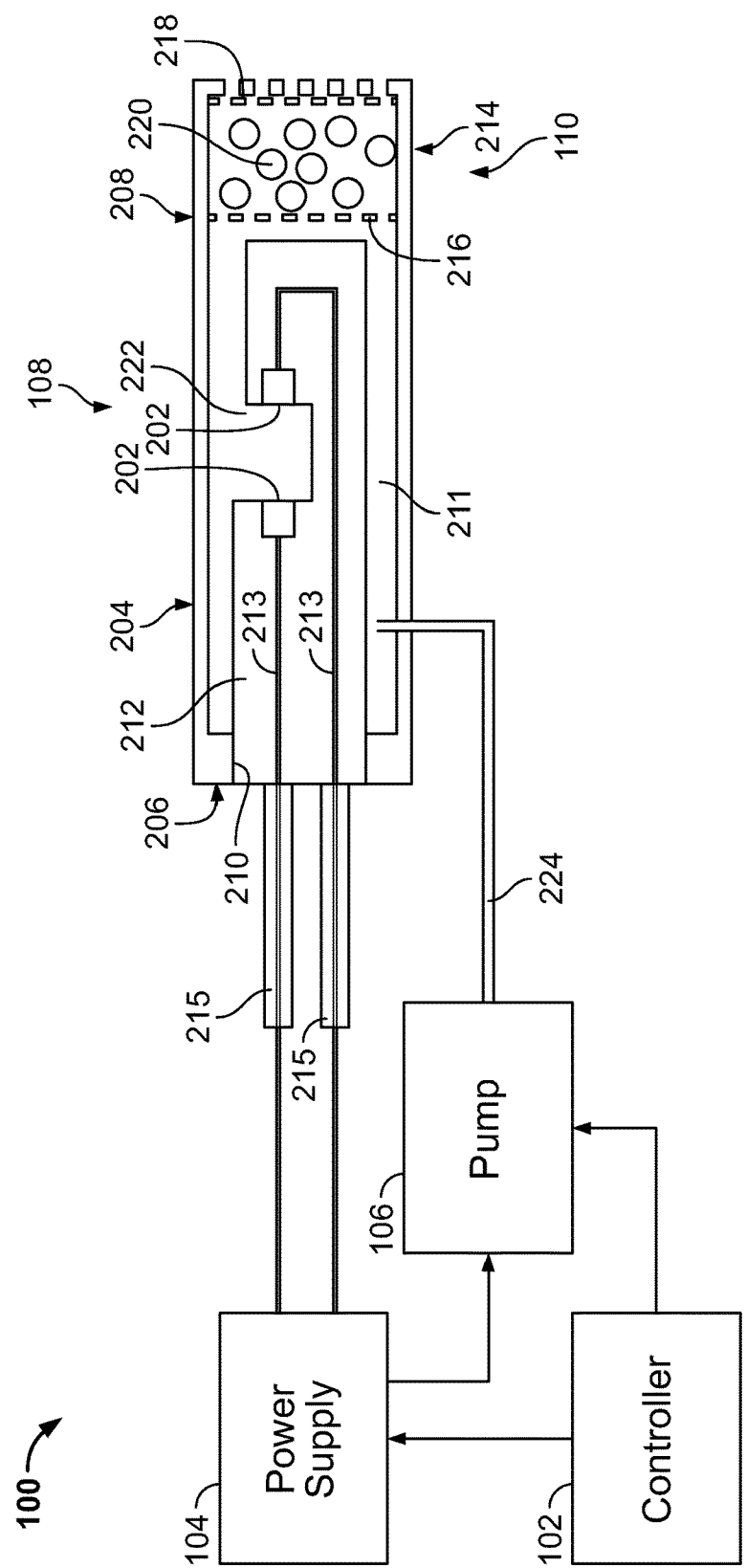
FIG. 3 is a detailed schematic of the nitric oxide generator of FIG. 2 with a tube entering radially into the generator according to one aspect of the present disclosure.
Figure 4:
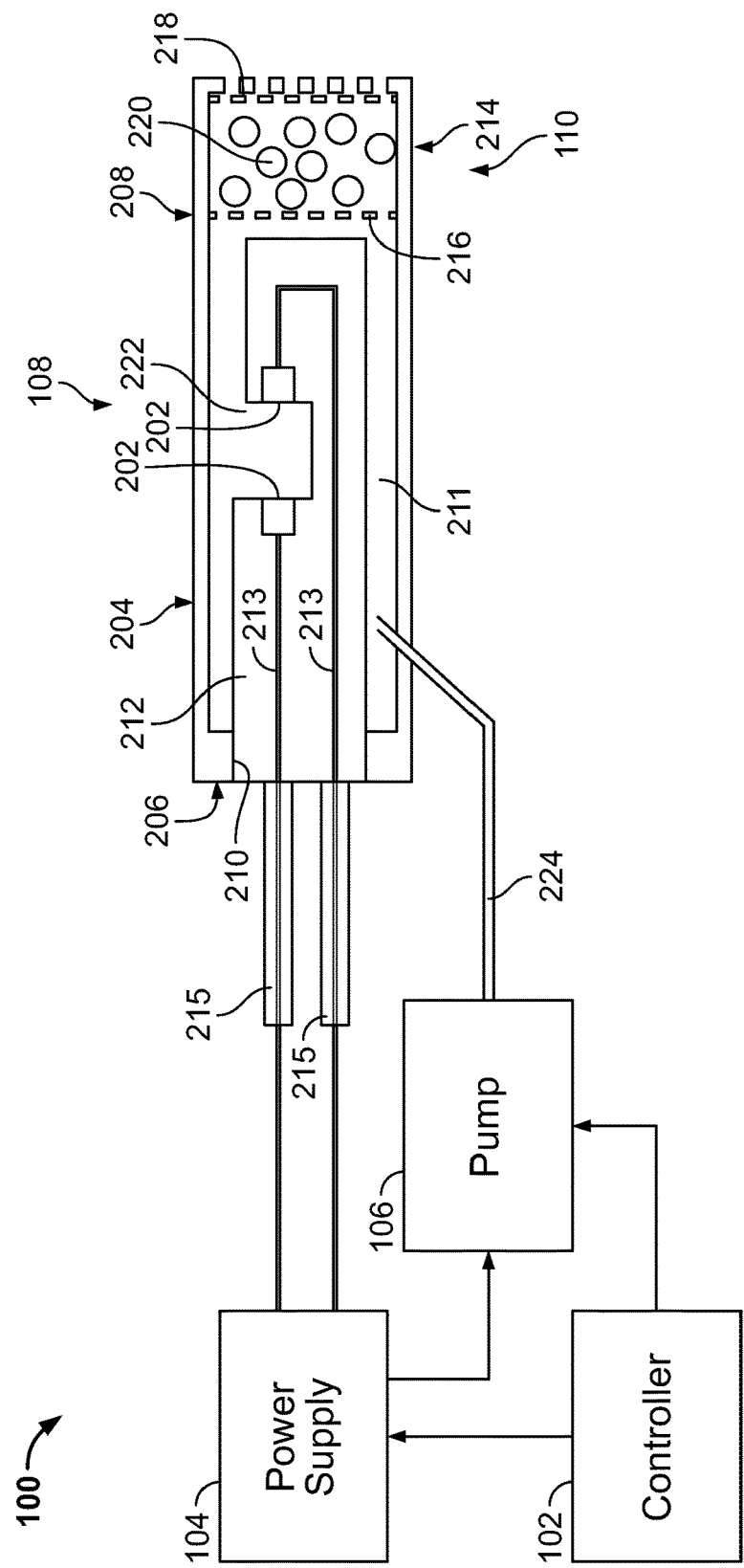
FIG. 4 is a detailed schematic of the nitric oxide generator of FIG. 2 with a tube entering at an angle into the generator according to one aspect of the present disclosure.

It should be appreciated that the orientation of the flow tube 224 with respect to the housing 204 and reaction chamber 222 may be configured to provide a desired flow pattern and/or swirl characteristics within the reaction chamber 222. For example, as illustrated in FIGS. 3 and 4, the flow tube 224 may extend radially through the housing 204 and into the reaction chamber 222 (FIG. 3), or the flow tube 224 may extend through the housing 204 and into the reaction chamber 222 at an angle (FIG. 4). In some non-limiting examples, an angle defined between the flow tube 224 and the outer surface of the housing 204 may be between approximately zero degrees and ninety degrees.

In some non-limiting examples, the pump 106 may be configured to furnish ambient air from the surrounding under increased pressure to the NO generator 108 via the flow tube 224. The air flow provided by the pump 106 into the reaction chamber 222 may act to convectively cool the NO generator 108 to maintain the NO generator 108 at or below temperatures safe for patient use and contact. In addition, the air flow provided by the pump 106 may act to provide fresh air into the reaction chamber to facilitate the generation of NO gas from the nitrogen and oxygen in ambient air. Further, the air flow provided by the pump 106 may facilitate the diffusion of freshly generated NO gas to the outlet of the NO generator 108 and thereby to the patient. Further still, the air flow provided by the pump 108 may aid in preventing a least a portion of exhaled $CO_2$ from reaching the scavenger 220. Generally, humans may release approximately 50,000 ppm of $CO_2$ during exhalation, and $CO_2$ may act to degrade the useful lifetime of the scavenger 220. Thus, it may be desirable to inhibit or prevent exhaled $CO_2$ from entering the NO generator 108. The NO generation system 100 is configured to limit the degradation of the scavenger 220 via exhaled $CO_2$ by triggering generation at or before inspiration, rather than continuously during the breathing cycle, and by supplying additional air flow into the reaction chamber 222 with the pump 108 and flow tube 224. The additional air flow provided by the pump 106 may act to generate a slightly positive pressure inside the reaction chamber 222, when compared to ambient, and inhibit flow back into the NO generator 108 thereby preventing at least a portion of exhaled $CO_2$ from reaching the scavenger 220.

Figure 5:
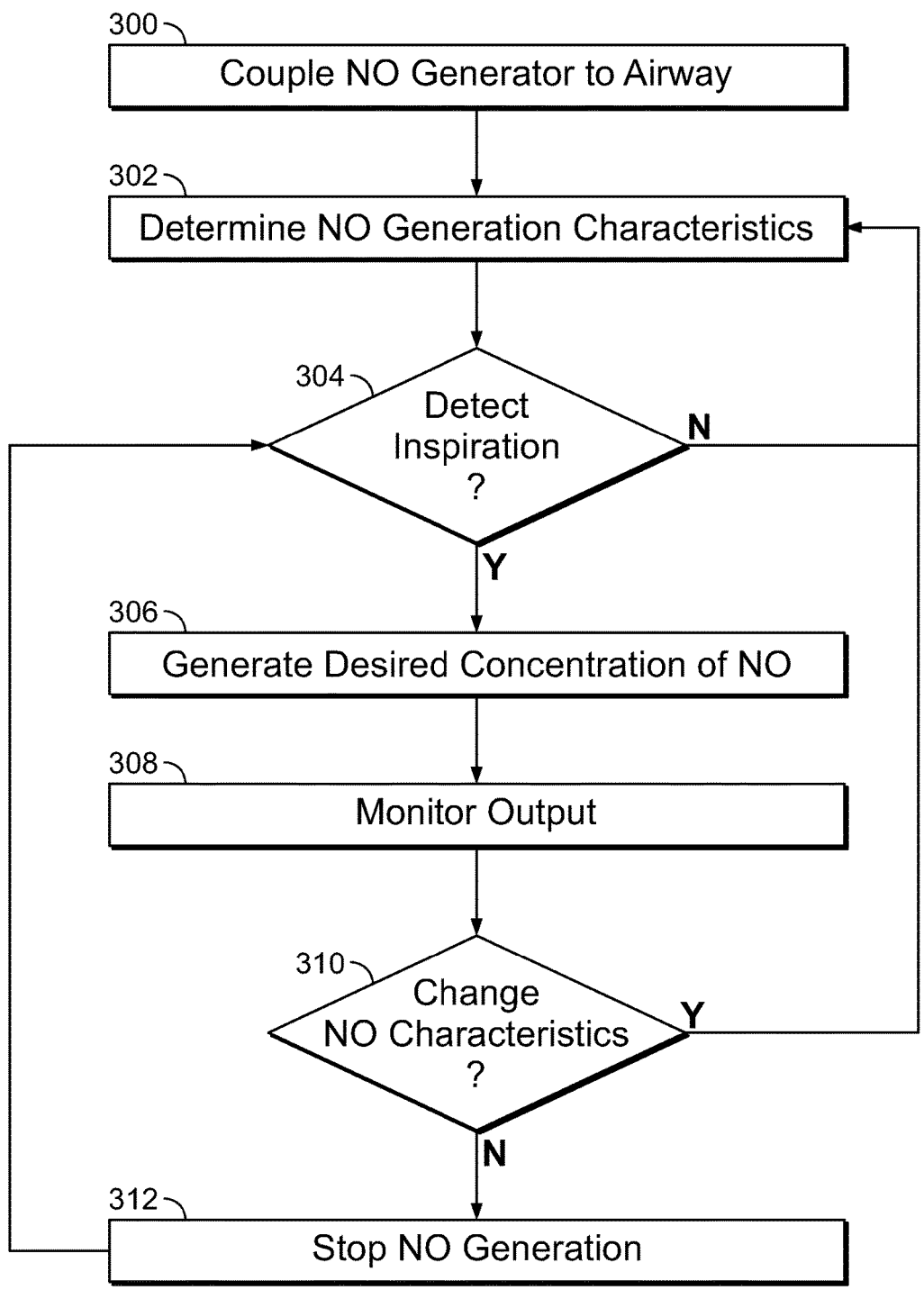
FIG. 5 is a flowchart outlining steps for operating the nitric oxide generation system of FIG. 1.

As described herein, the NO generation system 100 may be used to generate reliable and safe NO gas at the point-of-care, for example, for babies with hypoxia. One non-limiting example of the operation of the NO generation system 100 will be described with reference to FIGS. 1-5. Initially, as illustrated in FIG. 5, the NO generator 108 may be coupled to an airway of a patient at step 300. For example, the NO generator 108 may be assembled with the scavenger housing 214 attached to the housing 204 and the outlet of the NO generator 108 may be placed in fluid communication with an airway of a patient. In some non-limiting examples, the outlet of the NO generator 108 may be coupled to a ventilator. In some non-limiting examples, the outlet of the NO generator 108 may be coupled to a breathing tube placed in the airway of a patient.

Once the NO generator 108 is coupled to the airway of a patient at step 300, generation characteristics of the NO generator 108 may be determined at step 302. For example, a desired concentration of NO to be generated, an amount of time for NO to be generated after inspiration, a tidal volume, a body weight, a respiratory rate, ambient temperature, and ambient pressure, among other parameters, may be input and/or determined by the controller 102. Based on the operating parameters, for example, the controller 102 may determine the NO generation characteristics necessary to produce a desired amount of NO gas for a desired amount of time. In some non-limiting examples, the controller 102 may determine the necessary number of electrode discharge groups per second, the number of electrode discharges per group, a time (e.g., in microseconds) between adjacent electrode discharges within a group, and a pulse time (e.g., in microseconds) of each individual electrode discharge supplied to the electrodes 202 by the power supply 104. The characteristics determined by the controller 102 may be adjusted during operation, for example, to accommodate for output NO concentration, output $NO_2$ concentration, output $O_3$ concentration, ambient temperature, ambient pressure, NO generator 108 temperature, and/or measured biological parameters of the patient (e.g., ventricular systolic pressure, pulmonary artery pressure, etc.).

With the NO generation characteristics determined at step 302, it may be determined if an inspiration event of the patient is detected at step 304. In some non-limiting examples, the inspiration event may be detected by monitoring one or more breathing characteristics of a patient, such as, a fluid flow rate, temperature, pressure, oxygen ($O_2$) concentration, $CO_2$ concentration, thoracic volume, and/or ventilator operating parameters. If an inspiration event is detected at step 304, the NO generator 108 may be triggered to generate the desired concentration of NO gas for the desired amount of time after the detected inspiration event at step 306.

One or more output parameters of the NO generation system 100 may be monitored at step 308 and it may be determined at step 310 if the NO generation characteristics need to be changed based on the measured output parameters. For example, output NO concentration, output $NO_2$ concentration, output $O_3$ concentration, NO generator 108 temperature, and/or measured biological parameters of the patient (e.g., ventricular systolic pressure, pulmonary artery pressure, etc.) may be monitored by and/or input to the controller 102. In some non-limiting examples, the controller 102 may monitor one or more of the output parameters at step 308 and determine if one of the output parameters drifts outside a predetermined operating range and a change is needed at step 310. For example, the controller 102 may be configured to detect that the generated concentration of NO gas is not within a predetermined range of the desired concentration and, in response, alter one or more of the generation characteristics determined at step 302. Alternatively or additionally, the output concentration of $NO_2$ and/or $O_3$ may be monitored to determine if the scavenger 220 needs to be replaced. For example, a predetermined maximum concentration of $NO_2$ and/or $O_3$ for patient safety may be established and, once this predetermined maximum concentration is approached, it may be determined that the scavenger 220 is required to be replaced. Due to the removable attachment between the scavenger housing 214 and the housing 204, the scavenger 220 may be easily replaced by removing the current scavenger housing 214 and installing a new scavenger housing 214 with a new scavenger 220 arranged therein.

In some non-limiting examples, the temperature of the NO generator 108 may be monitored and it can be determined at step 310 if the pump 106 is supplying a sufficient flow of air thereto. For example, if the temperature of the NO generator 108 approaches a predetermined maximum value, the controller 102 may instruct the pump 106 to increase a flow rate of air supplied to the reaction chamber 222 to maintain the NO generator 108 at or below temperatures safe for patient use and contact. Alternatively or additionally, it may be determined at step 310 if NO gas has been generated for the desired amount of time. If so, the NO generator 108 may stop the generation of NO gas at step 312 and wait for the next, or another, inspiration event. In some non-limiting examples, the NO generation system 100 may be configured to instruct the NO generator 108 to stop generation of NO gas prior to the end of, or during, the inspiration of a patient.

The above-described steps 302-312 may be repeated for each inspiration event to continually supply reliable and safe NO-laden gas to a patient and maintain the NO generator 108 at a temperature that is safe for patient use and contact. Generally, the present disclosure provides a NO generation system 100 that utilizes a small fluid (e.g., gas) flow to cool down the NO generator 108 and, specifically the reaction chamber 222. Since the small fluid flow also facilitates the diffusion of generated NO, the need for high energy to produce desired levels of NO is negated. Thus, the present NO generation system 100 provides reduced energy consumption and also limits a temperature increase in the NO generator 108, without the need for high energy.

EXAMPLES

The following examples set forth, in detail, ways in which the NO generation system 100 and/or the NO generator 108 may be used or implemented, and will enable one of skill in the art to more readily understand the principles thereof. The following examples are presented by way of illustration and are not meant to be limiting in any way.

Test Setup and Prototype NO Generators

Figure 6:
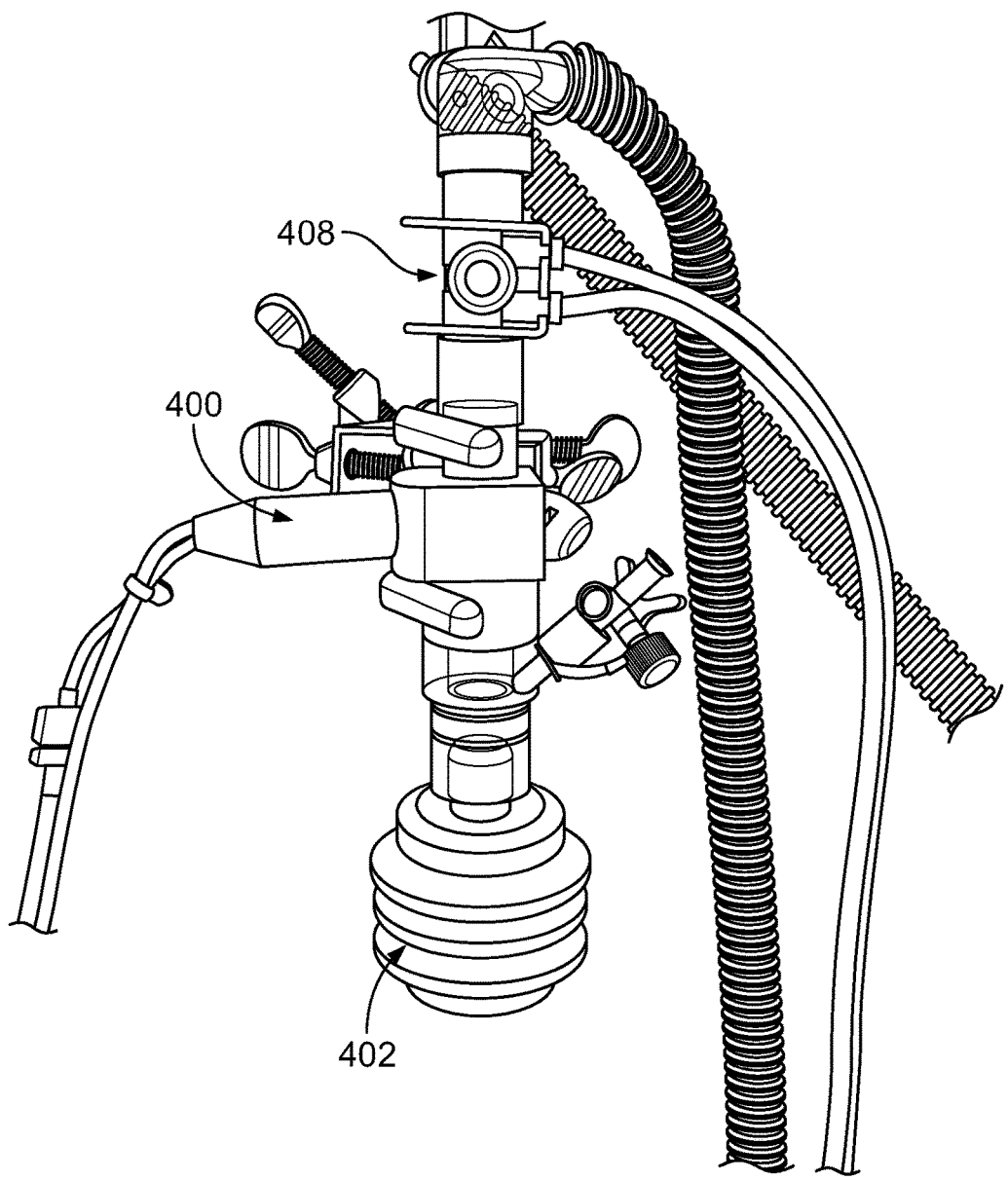
FIG. 6 is an illustration of a setup used to test the nitric oxide generation system of FIG. 1.
Figure 7:
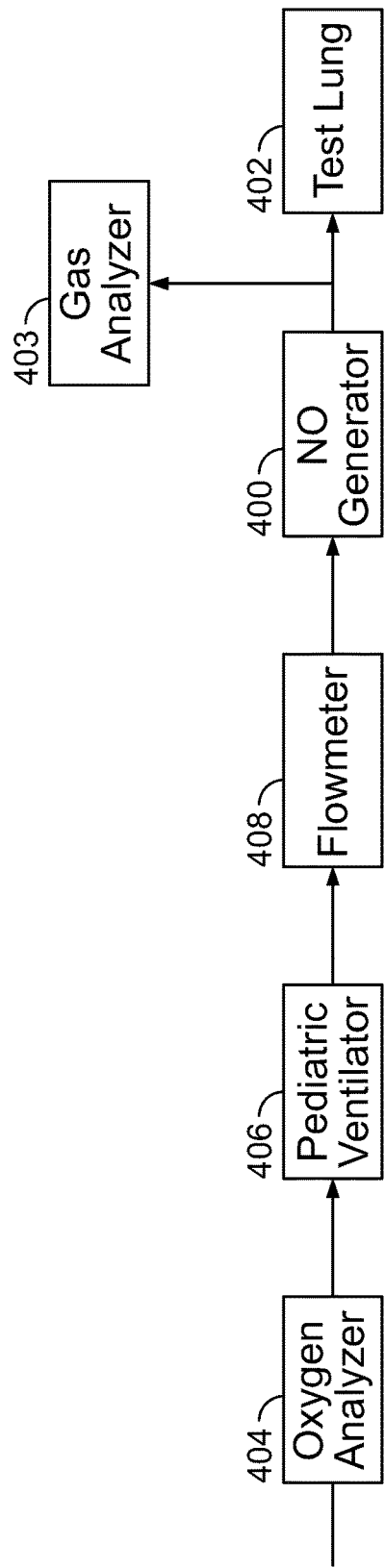
FIG. 7 is a schematic illustration of the test setup of FIG. 5.
Figure 8B:
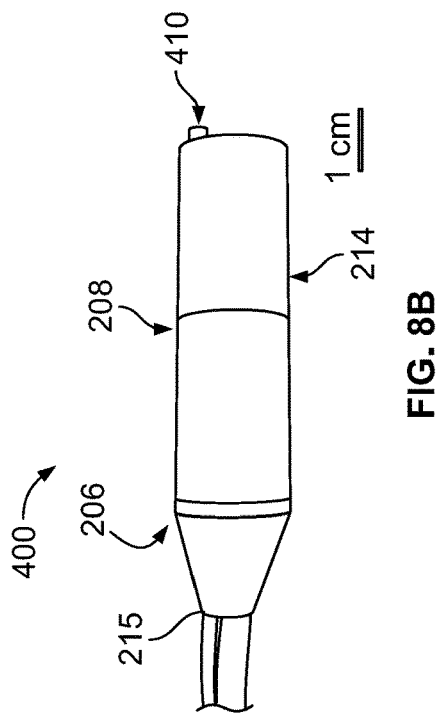
FIG. 8B is an illustration of a prototype of the nitric oxide generator of FIG. 2 with a 1.6 gram scavenger removably attached to a housing according to one aspect of the present disclosure.
Figure 8A:
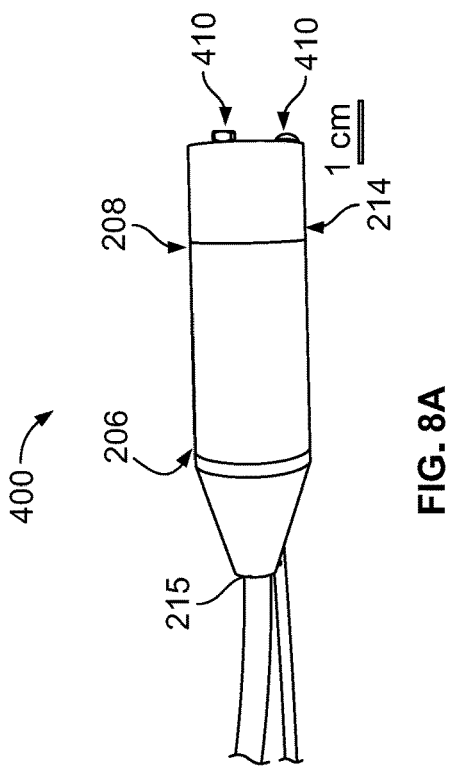
FIG. 8A is an illustration of a prototype of the nitric oxide generator of FIG. 2 with a 0.8 gram scavenger removably attached to a housing according to one aspect of the present disclosure.

FIGS. 6 and 7 illustrate a test setup used to test prototype NO generators (FIGS. 8A and 8B). As illustrated in FIGS. 6 and 7, a prototype NO generator 400 (e.g., a prototype of the NO generator 108 described herein) was placed in fluid communication with a test lung 402 arranged downstream of the prototype NO generator 400. A gas analyzer 403 was placed in between the prototype NO generator 400 and the test lung 402 to measure a concentration of NO (Sievers 280i Nitric Oxide Analyzer, GE Analytical Instruments, Boulder, Colo.), $NO_2$ (CAPS $NO_2$ monitor, Aerodyne Research Inc., Billerica, Mass.), and $O_3$ (EC 9810 Ozone Analyzer, American Ecotech, Warren, R.I.) being supplied to the test lung. Upstream of the prototype NO generator 400, an oxygen analyzer 404 (MiniOX I, Ohio Medical Corporation, Gurnee, Ill.) measured an input concentration of $O_2$, a pediatric ventilator 406 (Inspira asv, Harvard Apparatus, Holliston, Mass.) provided respiration to the test lung 402, and a flowmeter 408 (NICO2, Respironics) measured the fluid flow rate input to the prototype NO generator 400.

The prototype generators illustrated in FIGS. 8A and 8B were constructed with the wire insulator 215 attached to the first end 206 of the housing 204 and the scavenger housing 214 removably attached to the second end 208 of the housing 204 via a plurality of fastening elements 410 (e.g., screws or bolts). The prototype NO generator of FIG. 8A was constructed with a 0.8 g scavenger and weighed approximately 14 g. The prototype NO generator of FIG. 8B was constructed with a 1.6 g scavenger and weighted approximately 20 g. Thus, the constructed prototype NO generators are very lightweight, which aids in the portability thereof and the ability to provide NO-laden gas at the point-of-care.

Each of the prototype NO generators includes two iridium discharge electrodes, a scavenger comprising $Ca(OH)_2$, two 0.22 μm HEPA filters arranged on opposing ends of the scavenger, and a flow tube extending therein to facilitate cooling and NO delivery. These components were surrounded by a ceramic insulator, which was encased inside an aluminum housing. The electrodes were powered by a microcontroller circuit, and energy was stored and released by an autotransformer and delivered to the spark gap (2 mm) to create a plasma. The level of NO production was controlled by four pulse pattern variables, including the number of spark groups per second, the number of spark discharges per group, the time in microseconds (μsec) between two spark discharges, and the pulse time in μsec. During testing, the prototype NO generator was either sparked continuously or was triggered for sparking for 0.5 seconds at the commencement of each inspiration, as measured by the flowmeter 408.

Measurement of Voltage and Current Waveforms

During NO generation, waveforms of voltage across the spark gap and current through the iridium electrodes were captured and recorded by a digital phosphor oscilloscope (Tektronix DPO 2012B, Beaverton, Oreg.) equipped with a 1000× high voltage probe (Tektronix p6015A, Beaverton, Oreg.) and a current probe (I-prober 520, Aim & Thurlby Thandar Instruments Ltd, Cambridgeshire, UK). Voltage and current waveforms were measured and compared for the prototype NO generator of FIG. 8A at a tidal volume of 18 mL, a respiratory rate at 40 beats/minute (bpm), an airway $O_2$ level 50%, and an NO concentration at 40 ppm producing 40 pulses/second with a spark duration of 0.5 seconds. The electrodes were continuously cooled with 70 ml/min air which admixed with the 50% $O_2$ airway gas upstream of the prototype NO generator.

Figure 9:
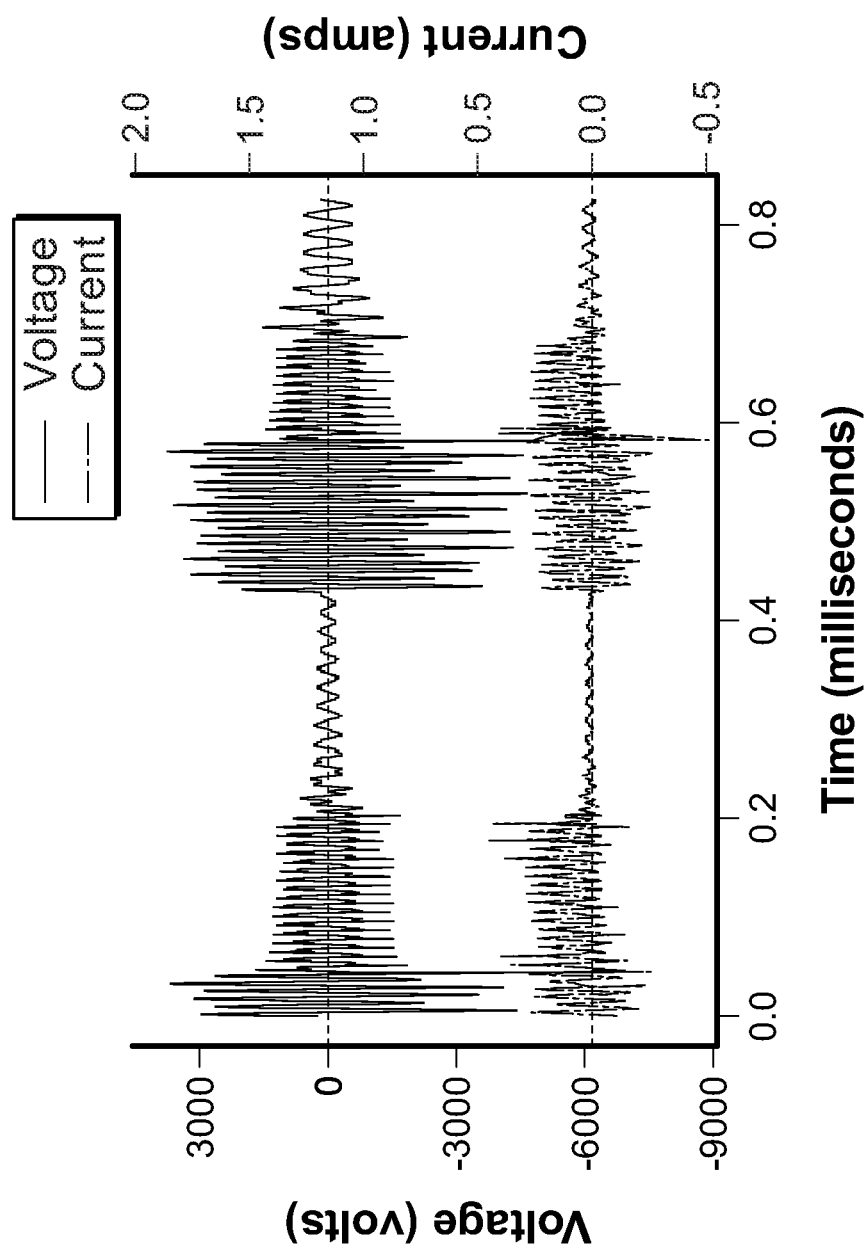
FIG. 9 is a graph illustrating a voltage and current waveforms as a function of time that were supplied to electrodes during testing of the prototypes of FIGS. 8A and 8B.

Typically, the voltage and current to initiate an electric arc are higher on the first arc than the following arcs. As illustrated in FIG. 9, the initial voltage was approximately 3 kV for each 0.5 second sparking event, and then exponentially decayed as the plasma formed and electrodes heated. Similarly, the initial current was approximately 200 mA, and then decayed gradually. The energy consumption was between approximately 2 and 3 Watts (W) for generating 40 ppm NO at tidal volume of 18 mL, respiratory rate at 40 bpm with airway $O_2$ level of 50%. The other components of the NO generation system, including the air pump, high-voltage overhead, and power supply, consume about 1.5 Watts energy. Thus, the NO generation system 100 described herein provides low power consumption, which aids in the portability thereof and the ability to provide NO-laden gas at the point-of-care.

Scavenging Capacity of the $Ca(OH)_2$ Scavenger

The scavenging capacity of the 0.8 g $Ca(OH)_2$ scavenger on the prototype NO generator of FIG. 8A was tested. During the test, the pediatric ventilator 406 was used to generate a tidal volume of 18 mL and a respiratory rate of 40 bpm. The airway $O_2$ level was set to 50% and the desired NO concentration was 40 ppm. The flowmeter sensed airway flow and triggered the prototype NO generator. The fraction of inspired oxygen ($FiO_2$) was measured at 0.48 due to injecting 70 ml/min of air via the air tube (ID=1.6 mm). $NO_2$ levels were measured and recorded every hour for the first 12 hours, and once at 24, 48, and 72 hours. Temperature changes of the aluminum housing of the prototype NO generator were measured with an infrared thermometer (Cole-Parmer, Vernon Hills, Ill.) every hour for the first 12 hours, and once at 24, 48, and 72 hours.

Figure 10:
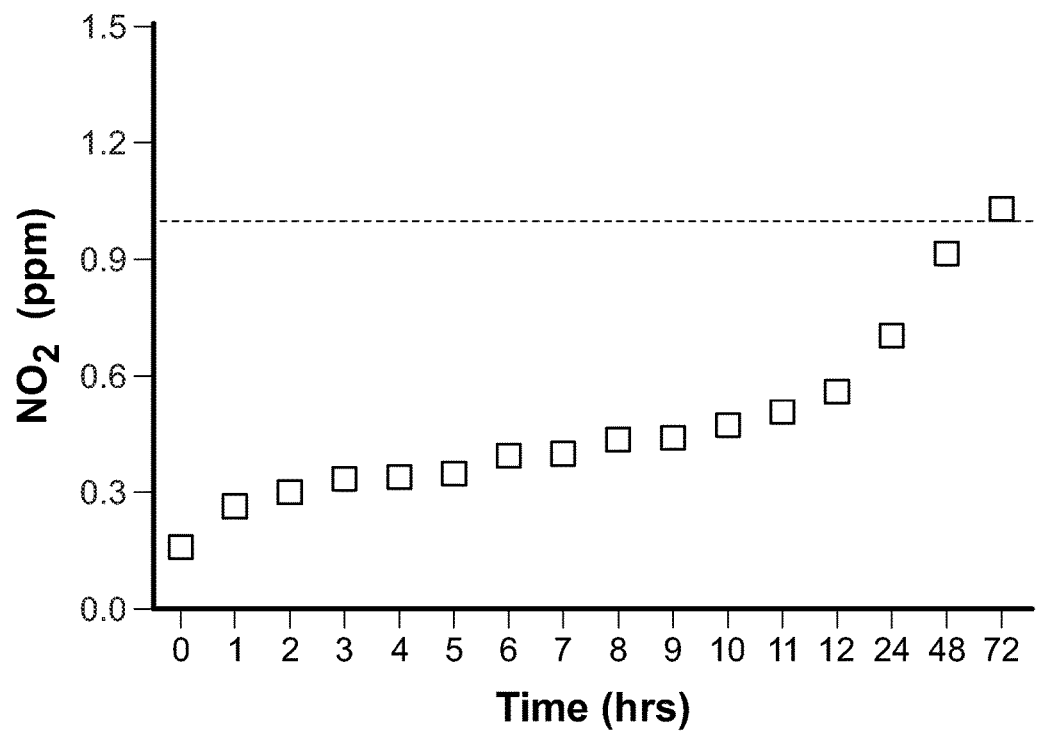
FIG. 10 is a graph illustrating nitrogen dioxide ($NO_2$) concentration generated by the prototype generator of FIG. 8A as a function of time during a three day test while generating 40 ppm of nitric oxide (NO).
Figure 11:
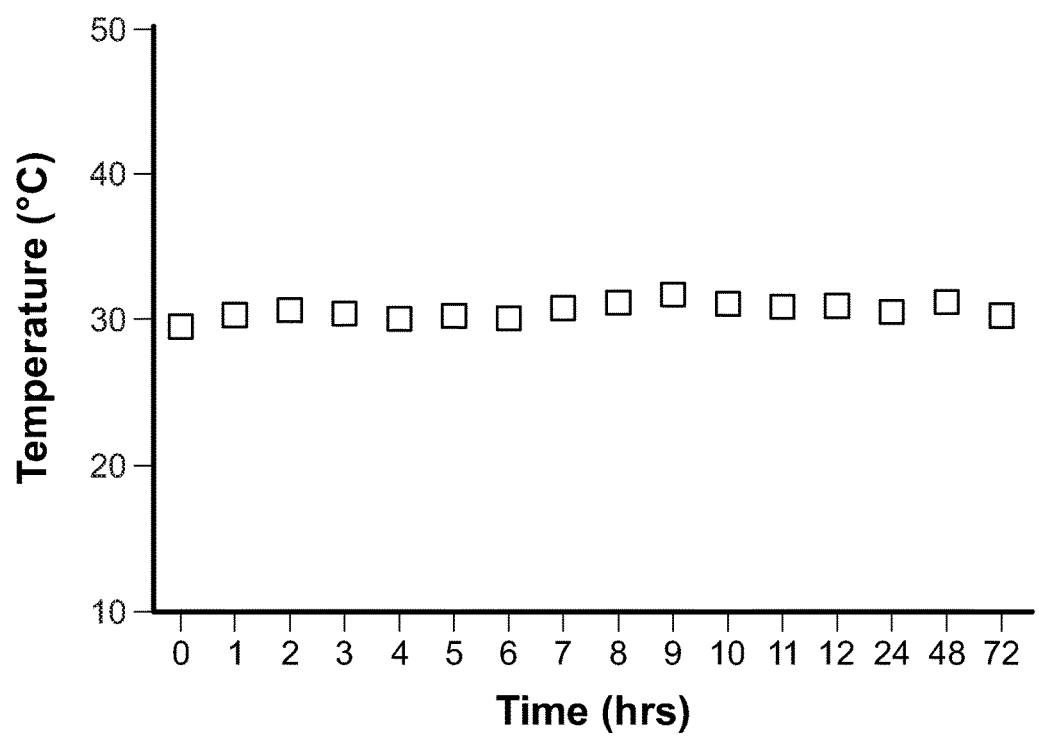
FIG. 11 is a graph illustrating a temperature of the prototype generator of FIG. 8A as a function of time during a three day test while generating 40 ppm of nitric oxide (NO).

As illustrated in FIGS. 10 and 11, the $NO_2$ levels were below 1 ppm for 48 hours, and the temperature was at 30.6±0.5° C. throughout the entire NO generation test. These data suggest that, with NO generation triggered on inspiration, 0.8 g of scavenger is sufficient to lower $NO_2$ levels for at least for 2 days, and the temperature of the spark chamber remained constant at approximately 31° C. for 3 days.

Ozone ($O_3$) Levels in the Effluent Gas with or without Scavenger

Figure 12A:
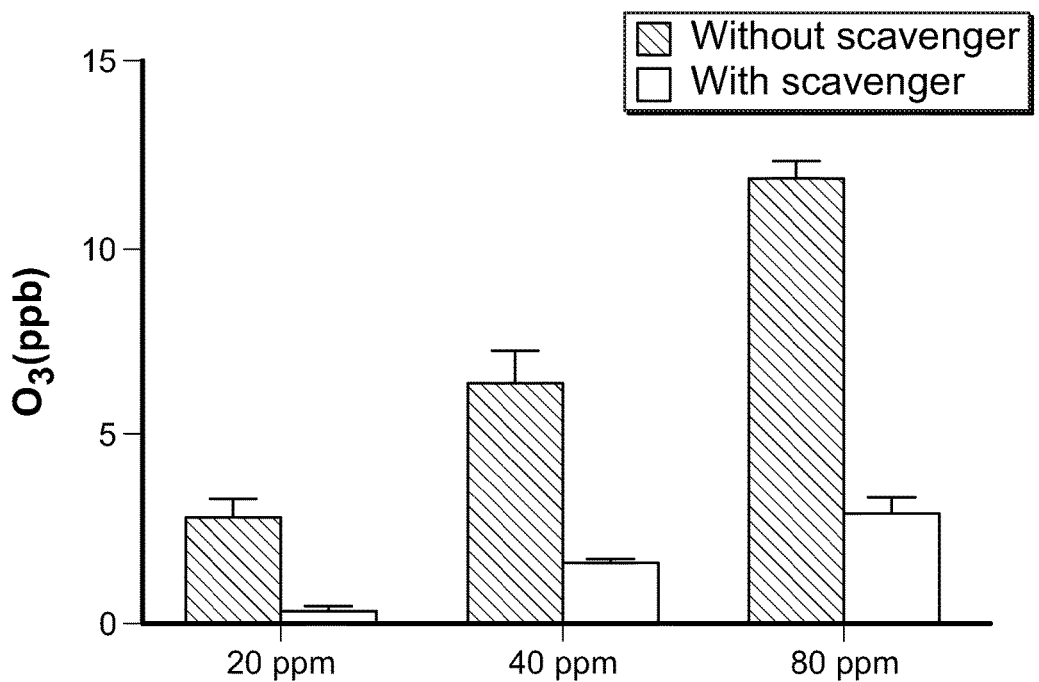
FIG. 12A is a graph illustrating ozone ($O_3$) concentration generated by the prototype generator of FIG. 8A with and without the 0.8 gram scavenger as a function of generated nitric oxide (NO) concentration.
Figure 12B:
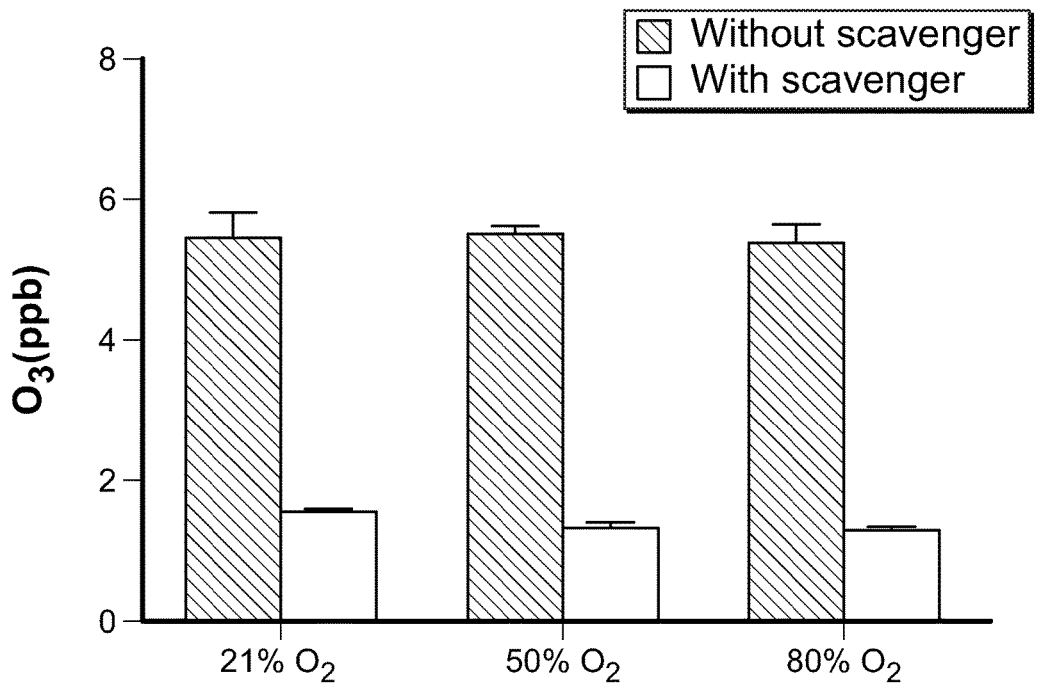
FIG. 12B is a graph illustrating ozone ($O_3$) concentration generated by the prototype generator of FIG. 8A with and without the 0.8 gram scavenger as a function of oxygen ($O_2$) concentration input to the prototype device.
Figure 12C:
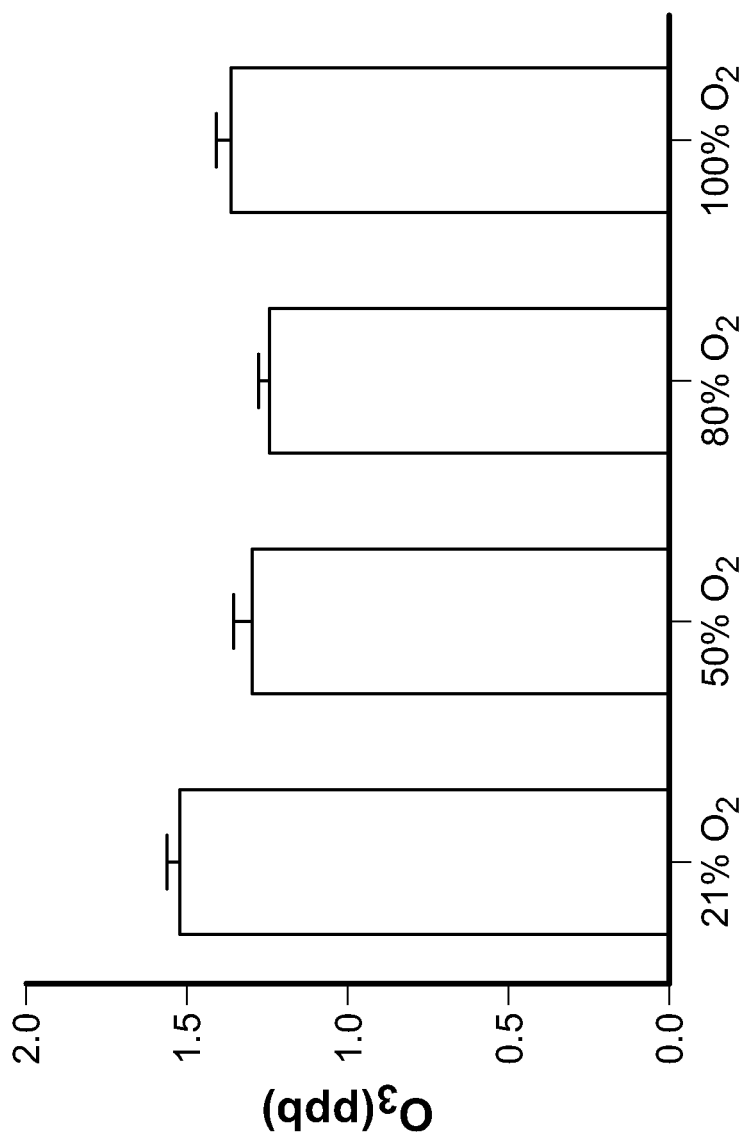
FIG. 12C is a graph illustrating ozone ($O_3$) concentration generated by the prototype generator of FIG. 8A with the 0.8 gram scavenger for various inspired oxygen concentrations ($FiO_2$).

An electrical discharge in $O_2$ may produce $O_3$ as a potential harmful byproduct. The $O_3$ levels produced by the prototype NO generator of FIG. 8A was measured at varying NO levels and $O_2$ levels, and the ability of the 0.8 g $Ca(OH)_2$ scavenger to remove $O_3$ was tested. As illustrated in FIG. 12A, at an airflow rate of 1 L/min, $O_3$ levels increased with increasing NO production. However, after passaging through the scavenger, $O_3$ level was reduced as low as 3 ppb with NO of 80 ppm. With varying $O_2$ levels from 21% to 80%, as illustrated in FIG. 12B, $O_3$ levels were at 5.5 ppb before and 1.5 ppb after scavenger. Also, as illustrated in FIG. 12C, the $O_3$ levels were kept below 1.5 ppb for all $O_2$ concentrations ranging from 21% to 100% at a gas flow rate of 1 L/min and a NO concentration of 40 ppm. This data suggests that the electrical prototype NO generator produces minimal amounts of $O_3$ at all $O_2$ concentrations tested, and the 0.8 g scavenger effectively removes $O_3$ to the levels well below U.S. Environmental Protection Agency (EPA) $O_3$ limits of 80 ppb exposure for 8 hours a day.

Trace Metals in Effluent Gas Downstream of Prototype NO Generator

To measure the levels of trace metals in the effluent gas downstream of the prototype NO generator of FIG. 8A, 5 groups were studied as follows: (1) without scavenger and HEPA filter, (2) with scavenger and 1 HEPA filter, (3) with scavenger and 2 HEPA filters in series, (4) with scavenger only, and (5) with 1 HEPA filter only. NO was generated at 40 ppm with airflow rate of 1 L/min for 24 hrs. The effluent gas was continuously bubbled into 15 ml of 5% nitric acid (Optima Grade, Fisher Scientific, Cambridge, Mass.). All samples were collected at 24 hours, and analyzed with quadrupole inductively-coupled mass spectrometry (ICP-MS) at University of Massachusetts Mass Spectrometry Center (Amherst, Mass.).

As illustrated in the table of FIG. 13, without a filter and scavenger, nickel particles at 40 ppb were produced by the plasma after 24 hours of NO generation at an airflow rate of 1 L/min. With an inline $Ca(OH)_2$ (0.8 g) scavenger, but without a HEPA filter, the nickel level was reduced to 1.7 ppb. With a single HEPA filter only, the nickel level was at 0.3 ppb. With the NO generator followed by a 0.8 g $Ca(OH)_2$ scavenger and one or two HEPA filters, nickel levels were reduced below 1 ppb, which is below the OSHA limit level of 1.0 mg/m$^3$ (mg/m$^3$=1 ppb) for metallic nickel and nickel compounds in workroom air in order to protect workers during an 8-hour shift over a 40-hour work week. The other trace metals of iridium and platinum were below 0.03 ppb with or without scavenger or HEPA filter, and can be ignored in the electrically generated NO gas. These data suggest that during NO generation trace amount of nickel would be released that can be effectively blocked by a scavenger and a HEPA filter.

Study of Anesthetized Rabbits with Pulmonary Hypertension

Rabbit studies were approved by the Massachusetts General Hospital Institutional Animal Care and Use Committee (Boston, Mass.). Five healthy 6-month-old male and female New Zealand White rabbits weighing 3.4±0.4 kg (mean±SD) (Jackson Laboratory, Bar Harbor, Me.). Rabbits were anesthetized (iv ketamine and fentanyl), paralyzed (rocuronium), and mechanically ventilated via tracheostomy at 6 ml/kg tidal volume, with respiratory rate 40-50 bpm, delivered airway $FiO_2$ 0.5, an inspiratory time of 0.5 seconds and PEEP 1-2 cm $H_2O$. Right ventricular systolic pressure (RVSP) was monitored continuously using a 4-Fr catheter (Swan-Ganz, Edwards Lifesciences, Irvine, Calif.) placed via external jugular vein. Pulmonary hypertension was induced by increasing right ventricular systolic pressure (RVSP) for 60 minutes infusing a potent pulmonary vasoconstrictor U46619 (Cayman Chemical, Ann Arbor, Mich.). Mean arterial pressure and heart rate were monitored at baseline, during U46619 infusion, and before and after breathing NO. The prototype NO generator of FIG. 8A was placed at the external end of tracheostomy tube (ID=3.5 mm), and NO was generated for 0.5 seconds on inspiration and triggered by the flowmeter 408.

Figure 14:
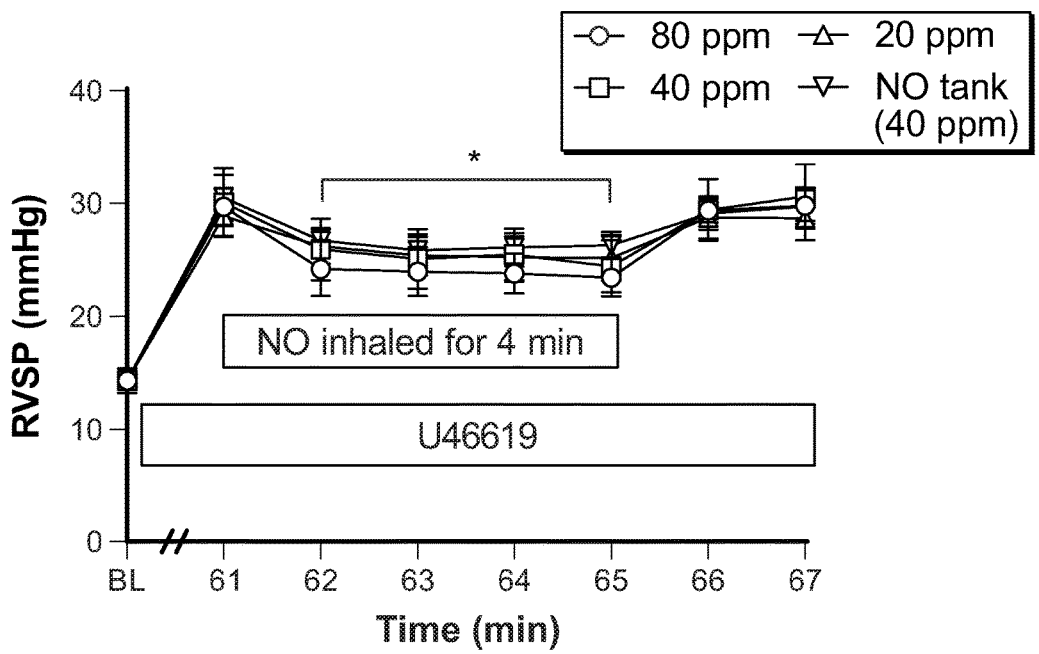
FIG. 14 is a graph illustrating a right ventricular systolic pressure (RVSP) as a function of time in anesthetized rabbits with acute pulmonary hypertension, due to U46619 infusion, inhaling various concentrations of nitric oxide (NO) generated by the prototype generator of FIG. 8A and inhaling 40 ppm nitric oxide (NO) from a $NO/N_2$ tank.
Figure 15:
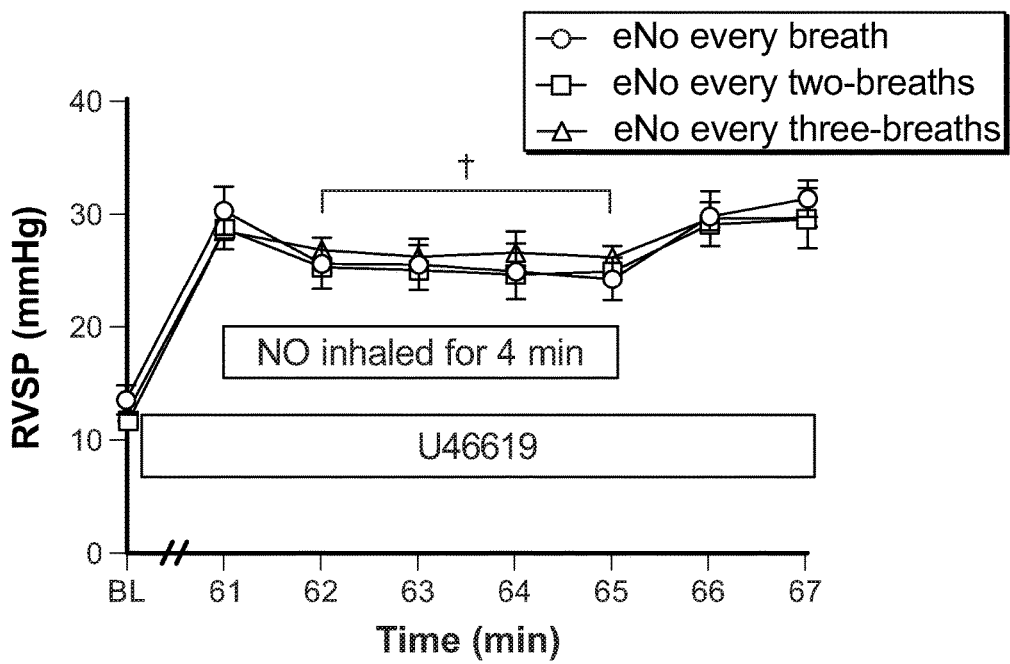
FIG. 15 is a graph illustrating a right ventricular systolic pressure (RVSP) as a function of time in anesthetized rabbits with acute pulmonary hypertension, due to U46619 infusion, inhaling 80 ppm of nitric oxide (NO) generated by the prototype generator of FIG. 8A triggered on every breath, every other breath, and every third breath.

In some non-limiting applications, the prototype NO generator may be designed for baby ventilation to treat pulmonary hypertension. NO generated from the prototype NO generator was compared it to the standard of care, NO from a $NO/N_2$ tank, to determine if the prototype NO would produce vasodilation in rabbits with acute pulmonary hypertension. As illustrated in FIGS. 14 and 15, anesthetized rabbits received a continuous infusion of the thromboxane analog U46619 over 60 mins, which increased RVSP from 14±2 mmHg to 28-30 mmHg. NO was generated by inspiratory plasma discharge, and then injected at 70 ml/min into the endotracheal tube. Rabbits breathed 50% $O_2$ and 20, 40, or 80 ppm NO produced on inspiration by the prototype NO generator for four minutes, then NO production and delivery were stopped, and RVSP was measured for an additional five minutes. With specific reference to FIG. 14, breathing electrically generated NO rapidly reduced the RVSP from 30 mmHg before NO breathing to 24 mmHg at one min after breathing NO. As a control, rabbits breathed 40 ppm NO diluted from a tank (500 ppm NO in $N_2$, Airgas, Cinnaminson, N.J.) in 50% $O_2$. This data indicates that electrically generated NO is as effective in reducing RVSP as breathing NO diluted from a convention $NO/N_2$ cylinder.

To save energy and reduce the consumption of the scavenger, it was tested whether sparking every two- or three-breaths on inspiration would reduce RVSP in rabbits with pulmonary hypertension. As illustrated in FIG. 15, NO generated on every two- or three-breaths reduced RVSP from 30 mmHg to 26 mmHg in rabbits (P<0.05 differ versus before NO breathing), which indicates that triggering on every two- or three-breaths may be effective in treating pulmonary hypertension and reduce the power consumption of the NO generation system 100 and increase the lifetime of the scavenger 220.

Within this specification embodiments have been described in a way which enables a clear and concise specification to be written, but it is intended and will be appreciated that embodiments may be variously combined or separated without parting from the invention. For example, it will be appreciated that all preferred features described herein are applicable to all aspects of the invention described herein.

Thus, while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

We claim:

1. A nitric oxide (NO) generation system comprising:
a nitric oxide generator including:
a housing including a first end and a generally open second end;
a pair of electrodes enclosed within the housing; and
a reaction chamber defined between the pair of electrodes and the housing;
a scavenger housing including a scavenger and a filter arranged therein, wherein the scavenger housing is configured to be removably attached to the second end of the housing;
a power supply connected to the pair of electrodes;
a pump configured to provide fluid flow;
a controller in communication with the pump and the power supply, wherein the controller is configured to selectively instruct the power supply to provide power to the pair of electrodes to generate one or more electric discharges therebetween to generate nitric oxide within the reaction chamber;
and
a flow tube configured to provide fluid communication between the pump and the reaction chamber, wherein the fluid flow provided from the pump to the reaction chamber is configured to cool the nitric oxide generator and aid in diffusion of the generated nitric oxide from the reaction chamber.

2. The nitric oxide generation system of claim 1, wherein the pair of electrodes comprise at least one of tungsten carbide, carbon, iridium, titanium, rhenium, and platinum.

3. The nitric oxide generation system of claim 1, wherein the pair of electrodes comprise iridium.

4. The nitric oxide generation system of claim 1, wherein the scavenger is fabricated from calcium hydroxide.

5. The nitric oxide generation system of claim 1, wherein the scavenger is configured to control an amount of undesired byproducts from the one or more electric discharges between the pair of electrodes.

6. The nitric oxide generation system of claim 1, wherein the power supply comprises a resonant power supply.

7. The nitric oxide generation system of claim 1, wherein the scavenger housing further comprises a second filter, and wherein the scavenger is arranged between the filter and the second filter.

8. The nitric oxide generation system of claim 7, wherein the filter and the second filter are each configured to filter particles with a diameter greater than approximately 0.22 micrometers.

9. The nitric oxide generation system of claim 7, wherein the filter and the second filter each comprise a HEPA filter.

10. The nitric oxide generation system of claim 7, wherein the filter is configured to filter electrode particles upstream of an airway of a patient and to prevent granular scavenger from entering the reaction chamber, and the second filter is configured to filter electrode particles upstream of the airway of the patient.

11. The nitric oxide generation system of claim 1, wherein the second end of the housing includes a second filter coupled thereto.

12. The nitric oxide generation system of claim 11, wherein the filter and the second filter are each configured to filter particles with a diameter greater than approximately 0.22 micrometers.

13. The nitric oxide generation system of claim 11, wherein the filter and the second filter each comprise a HEPA filter.

14. The nitric oxide generation system of claim 11, wherein the filter is configured to filter electrode particles upstream of an airway of a patient and to prevent granular scavenger from entering the reaction chamber, and the second filter is configured to filter electrode particles upstream of the airway of the patient.

15. The nitric oxide generation system of claim 1, further comprising a temperature sensor arranged to measure at least one of a temperature of the nitric oxide generator and a temperature of nitric oxide-laden gas output from the scavenger housing.

16. The nitric oxide generation system of claim 15, wherein the controller is further configured to selectively control a fluid flow rate provided by the pump in response to the temperature measured by the temperature sensor.

17. The nitric oxide generation system of claim 1, wherein the controller is configured to detect an inspiration event.

18. The nitric oxide generation system of claim 17, wherein the controller is further configured to instruct the power supply to provide power to the pair of electrodes to generate one or more electric discharges therebetween in response to the detection of the inspiration event.

19. The nitric oxide generation system of claim 18, wherein the controller is further configured to instruct the power supply to provide power to the pair of electrodes for a predetermined amount of time.

20. The nitric oxide generation system of claim 1, wherein the scavenger weighs less than approximately 2 grams.

21. The nitric oxide generation system of claim 1, wherein the scavenger weighs less than 1 gram.

22. The nitric oxide generation system of claim 1, wherein the scavenger weighs approximately 0.8 grams.

23. An apparatus for generating nitric oxide (NO) comprising:
  a housing including a first end, a generally open second end, and a cavity arranged between the first end and the second end;
  a pair of electrodes arranged within the cavity of the housing;
  a reaction chamber defined between the pair of electrodes and the housing, wherein the pair of electrodes are configured to generate one or more electric discharges therebetween to generate nitric oxide within the reaction chamber;
  a scavenger housing including a scavenger and a filter arranged therein, wherein the scavenger housing is configured to be removably attached to the second end of the housing; and
  a flow tube extending through the housing and into the reaction chamber to provide fluid communication between a pump and the reaction chamber, wherein fluid flow provided from the pump to the reaction chamber is configured to cool the nitric oxide generator and aid in diffusion of the generated nitric oxide from the reaction chamber.

24. The apparatus of claim 23, wherein the pair of electrodes comprise at least one of tungsten carbide, carbon, iridium, titanium, rhenium, and platinum.

25. The apparatus of claim 23, wherein the pair of electrodes comprise iridium.

26. The apparatus of claim 23, wherein the scavenger is fabricated from calcium hydroxide.

27. The apparatus of claim 23, wherein the scavenger is configured to control an amount of undesired byproducts from the one or more electric discharges between the pair of electrodes.

28. The apparatus of claim 23, further comprising a power supply connected to the pair of electrodes, and wherein the power supply comprises a resonant power supply.

29. The apparatus of claim 23, wherein the scavenger housing further comprises a second filter, and wherein the scavenger is arranged between the filter and the second filter.

30. The apparatus of claim 29, wherein the filter and the second filter are each configured to filter particles with a diameter greater than approximately 0.22 micrometers.

31. The apparatus of claim 29, wherein the filter and the second filter each comprise a HEPA filter.

32. The apparatus of claim 29, wherein the filter is configured to filter electrode particles upstream of an airway of a patient and to prevent granular scavenger from entering the reaction chamber, and the second filter is configured to filter electrode particles upstream of the airway of the patient.

33. The apparatus of claim 23, wherein the second end of the housing includes a second filter coupled thereto.

34. The apparatus of claim 33, wherein the filter and the second filter are each configured to filter particles with a diameter greater than approximately 0.22 micrometers.

35. The apparatus of claim 33, wherein the filter and the second filter each comprise a HEPA filter.

36. The apparatus of claim 33, wherein the filter is configured to filter electrode particles upstream of an airway of a patient and to prevent granular scavenger from entering the reaction chamber, and the second filter is configured to filter electrode particles upstream of the airway of the patient.

37. The apparatus of claim 23, further comprising a temperature sensor arranged to measure at least one of a temperature of the nitric oxide generator and a temperature of nitric oxide-laden gas output from the scavenger housing.

38. The apparatus of claim 23, wherein a controller is configured to selectively control a fluid flow rate provided by the pump in response to the temperature measured by the temperature sensor.

39. The apparatus of claim 23, wherein a controller is configured to detect an inspiration event.

40. The apparatus of claim 39, wherein the controller is further configured to instruct a power supply to provide power to the pair of electrodes to generate one or more electric discharges therebetween in response to the detection of the inspiration event.

41. The apparatus of claim 40, wherein the controller is further configured to instruct the power supply to provide power to the pair of electrodes for a predetermined amount of time.

42. The apparatus of claim 23, wherein the scavenger weighs less than approximately 2 grams.

43. The apparatus of claim 23, wherein the scavenger weighs less than 1 gram.

44. The apparatus of claim 23, wherein the scavenger weighs approximately 0.8 grams.

* * * * *